(12) United States Patent
Bachand et al.

(10) Patent No.: US 11,854,669 B1
(45) Date of Patent: Dec. 26, 2023

(54) SYNTHETIC NUCLEIC ACIDS FOR INFORMATION STORAGE AND TRANSMISSION

(71) Applicant: National Technology & Engineering Solutions of Sandia, LLC, Albuquerque, NM (US)

(72) Inventors: George Bachand, Albuquerque, NM (US); Marlene Bachand, Albuquerque, NM (US); Andrew Gomez, Edgewood, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 1197 days.

(21) Appl. No.: 16/512,577

(22) Filed: Jul. 16, 2019

Related U.S. Application Data

(60) Provisional application No. 62/711,964, filed on Jul. 30, 2018.

(51) Int. Cl.
    *G16B 50/40* (2019.01)
    *H04L 9/08* (2006.01)

(52) U.S. Cl.
    CPC ............ *G16B 50/40* (2019.02); *H04L 9/0866* (2013.01)

(58) Field of Classification Search
    None
    See application file for complete search history.

(56) References Cited

U.S. PATENT DOCUMENTS

| | | | |
|---|---|---|---|
| 6,312,911 B1 * | 11/2001 | Bancroft ................ | G06N 3/123 435/6.11 |
| 9,384,320 B2 | 7/2016 | Church | |
| 2015/0038373 A1 | 2/2015 | Banyal et al. | |
| 2015/0261664 A1 | 9/2015 | Goldman et al. | |
| 2016/0090592 A1 | 3/2016 | Banyal et al. | |
| 2017/0338843 A1 | 11/2017 | Lu et al. | |
| 2019/0325040 A1 * | 10/2019 | Sagi .................... | G06F 16/1748 |

OTHER PUBLICATIONS

Nguyen et al. Long-Term Stability and Integrity of Plasmid-Based DNA Data Storage Polymers vol. 10, article 28 (Year: 2018).*
Wikipedia Polymerase Chain Reaction https://en.wikipedia.org/wiki/Polymerase_chain_reaction Accessed on Aug. 12, 2022 (Year: 2022).*
Adleman LM, "Molecular computation of solutions to combinatorial problems," *Science* 1994:266(5187):1021-4.
Akhavan A et al., "Cryptanalysis of an image encryption algorithm based on DNA encoding," *Optics Laser Technol.* 2017;95:94-9.
Artz D, "Digital steganography: hiding data within data," *IEEE Internet Comput.* 2001;5(3):75-80.
Awad A et al., "A new image encryption algorithm based on a chaotic DNA substitution method," IEEE International Conference on Communications (ICC), held on Jun. 10-15, 2012 in Ottawa, Ontario, Canada, pp. 1011-1015.
Babaei M. "A novel text and image encryption method based on chaos theory and DNA computing," *Nat. Comput.* 2013;12(1):101-7.
Bancroft C et al., "Long-term storage of information in DNA," *Science* 2001;293(5536):1763-5.
Biswas MR et al., "A DNA cyrptographic technique based on dynamic DNA encoding and asymmetric cryptosystem," 4th International Conference on Networking, Systems and Security (NSysS), held on Dec. 18-20, 2017 in Dhaka, Bangladesh (8 pp.).
Bornholt J et al., "A DNA-based archival storage system," Proceedings of the 21st International Conference on Architectural Support for Programming Languages and Operating Systems (ASPLOS'16), held on Apr. 2-6, 2016 in Atlanta, Georgia, pp. 637-649.
Cello J et al., "Chemical synthesis of poliovirus cDNA: generation of infectious virus in the absence of natural template," *Science* 2002;297(5583):1016-8.
Chai X et al., "A novel chaos-based image encryption algorithm using DNA sequence operations," *Optics Laser Eng.* 2017;88:197-213.
Church GM et al., "Next-generation digital information storage in DNA," *Science* 2012;337:1628.
Church GM et al., Supplementary Materials for "Next-generation digital Information storage in DNA," *Science* 2012;337:1628 (16 pp.).
Clelland CT et al., "Hiding messages in DNA microdots," *Nature* 1999;399:533-4.
Clelland CT et al., Supplementary Information for "Hiding messages in DNA microdots," *Nature* 1999:399:533-4 (13 pp.).
Cline J et al., "PCR fidelity of Plu DNA polymerase and other thermostable DNA polymerases," *Nucl. Acids Res.* 1996;24(18):3546-51.
Cui G et al., "An encryption scheme using DNA technology," 3rd International Conference on Bio-Inspired Computing: Theories and Applications, held on Sep. 28-Oct. 1, 2008 in Adelaide, SA, Australia, pp. 37-41.
Dou Y et al., "Cryptanalysis of a DNA and chaos based image encryption algorithm," *Optik* 2017;145:456-64.
Gibson DG et al., "Enzymatic assembly of DNA molecules up to several hundred kilobases," *Nat. Methods* 2009;6:343-5.
Gibson DG et al., "Complete chemical synthesis, assembly, and cloning of a *Mycoplasma genitalium* genome," *Science* 2008;319(5867):1215-20.
Gibson DG et al., "Chemical synthesis of the mouse mitochondrial genome," *Nat. Methods* 2010;7(11):901-3.
Goldman N et al., "Towards practical, high-capacity, low-maintenance information storage in synthesized DNA," *Nature* 2013;494(7435):77-80.

(Continued)

*Primary Examiner* — John S Brusca
*Assistant Examiner* — Joseph Pulliam
(74) *Attorney, Agent, or Firm* — Helen S. Baca; Eschweiler & Potashnik LLC

(57) ABSTRACT

The present invention relates to method for storing and transmitting information by employing a nucleic acid construct. The nucleic acid construct can include a lock region; a translation key region that corresponds to the identity of a key; and a message region including a nucleic sequence that corresponds to an encrypted message.

20 Claims, 19 Drawing Sheets
Specification includes a Sequence Listing.

(56) References Cited

OTHER PUBLICATIONS

Goldman N et al., Supplementary Information 1 for "Towards practical, high-capacity, low-maintenance information storage in synthesized DNA," *Nature* 2013;494(7435):77-80 (17 pp.).

Goldman N et al., Supplementary Information 2 for "Towards practical, high-capacity, low-maintenance information storage in synthesized DNA." *Nature* 2013;494(7435):77-80 (6 pp.).

Grass RN et al., "Robust chemical preservation of digital information on DNA in silica with error-correcting codes," *Agnew. Chem. Int. Ed.* 2015;54:2552-5.

Hayden EC, "The $1,000 genome," *Nature* 2014;507:294-5.

Hu T et al., "An image encryption scheme combining chaos with cycle operations for DNA sequences," *Nonlinear Dyn.* 2017;87:51-66.

Kieleczawa J et al., "Optimization of protocol for sequencing of difficult templates," *J. Biomol. Tech.* 2010:21(2):97-102.

Kircher M et al., "High-throughput DNA sequencing-concepts and limitations," *Bioessays* 2010;32(6):524-36.

Kosuri S et al., "Large-scale de novo DNA synthesis: technologies and applications," *Nat. Methods* 2014;11:499-507.

Leake D, "DNA synthesis steps up," *Genetic Engineering & Biotechnology News* 36(8), Aug. 15, 2016 (3 pp.).

Leier A et al., "Cryptography with DNA binary strands," *BioSystems* 2000;57:13-22.

Liu L et al., "A RGB image encryption algorithm based on DNA encoding and chaos map," *Comput. Electr. Eng.* 2012;38(5):1240-8.

Metzker ML, "Sequencing technologies—the next generation," *Nat. Rev. Genet.* 2010;11:31-46.

Orlando L et al., "Recalibrating Equus evolution using the genome sequence of an early Middle Pleistocene horse," *Nature* 2013;499:74-8.

Palmer R, "Companies hope to bring DNA storage in from the cold," *Nat. Med.* 2010;16:1056-7.

Paul S et al., "Secured image encryption scheme based on DNA encoding and chaotic map," *Rev. Comput. Eng. Studies* 2017;4(2):70-5.

Rappe M, "Sandia storing information securely in DNA," *Sandia Labs News Release*, Jul. 11, 2016 (4 pp.).

Saeed Al-Waitar AH et al., "Review of DNA and pseudo DNA cryptography," *Int. J. Comput. Sci. Eng.* 2015;4(4):65-76.

Strickland E, "Microsoft buys into DNA storage," *IEEE Spectrum*, Apr. 27, 2016 (2 pp.).

Twist Bioscience, "Twist Bioscience announces Microsoft purchase of its synthetic DNA for digital storage research," *Press Release*, Apr. 27, 2016 (3 pp.).

Yazdi SMHT et al., "A rewritable, random-access DNA-based storage system," *Sci. Rep.* 2015;5:14138 (10 pp.).

Yazdi SMHT et al., "DNA-based storage: trends and methods," *IEEE Trans. Molec. Biol. Multi-scale Commun.* 2015:1(3):230-48.

Zhang Q et al., "DNA coding and chaos-based image encryption algorithm," *J. Comput. Theor. Nanosci.* 2013;10(2):341-6.

Zhang Y et al., "An optimized DNA based encryption scheme with enforced secure key distribution," *Cluster Comput.* 2017;20:3119-30.

Zhang Y, "The image encryption algorithm based on chaos and DNA computing," *Multimed. Tools. Appl.* 2018; 77(16): 21589-615.

Zhirnov V et al., "Nucleic acid memory," *Nature Mater*. 2106;15:366-70, 2016.

* cited by examiner

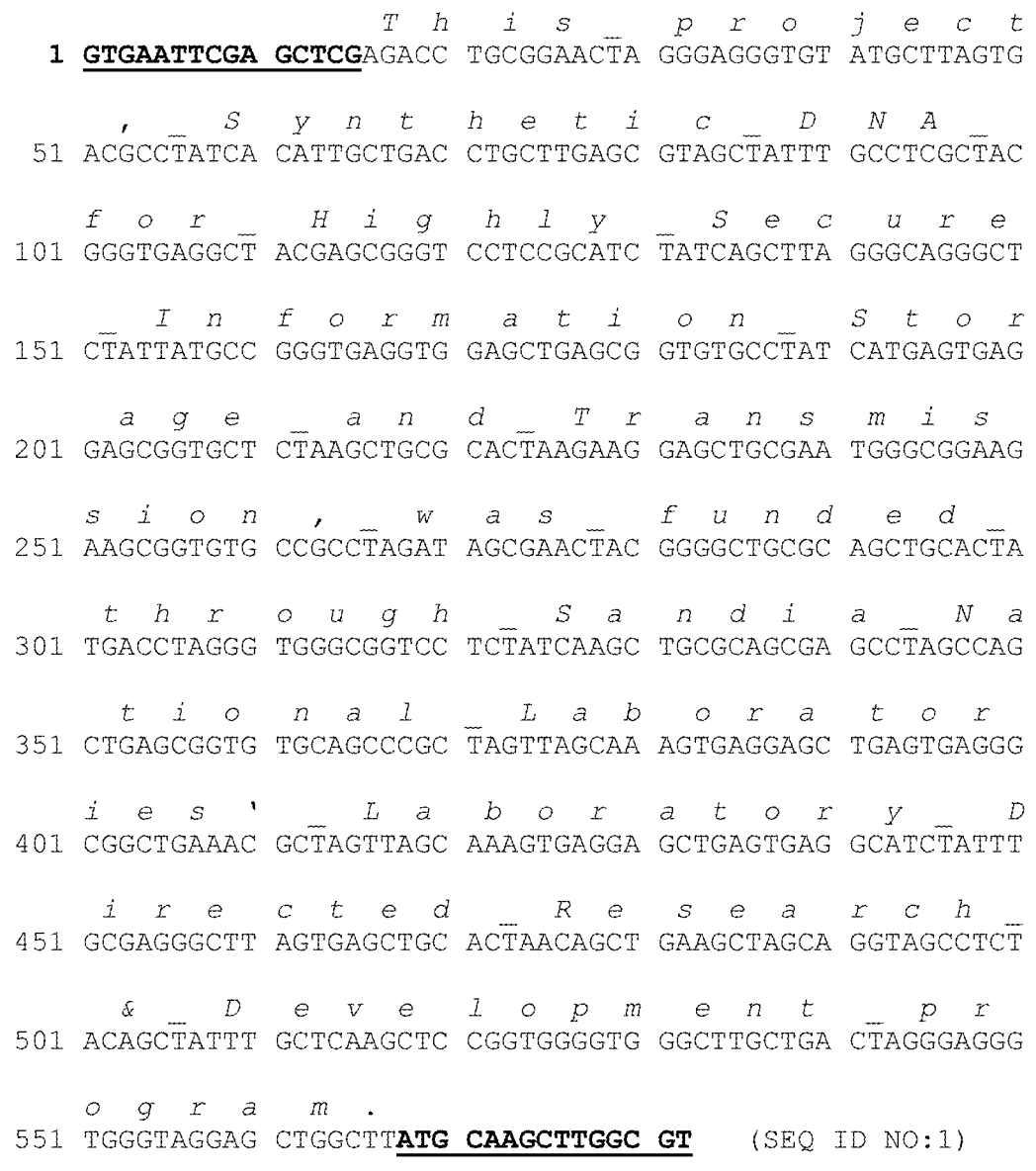

```
                           T  h  i  s  _  p  r  o  j  e  c  t
  1 GTGAATTCGA GCTCGAGACC TGCGGAACTA GGGAGGGTGT ATGCTTAGTG

,  _  S  y  n  t  h  e  t  i  c  _  D  N

```
  1 GTGAATTCGA GCTCGAGACC TGCGGAACTA GGGAGGGTGT ATGCTTAGTG
  1 CACTTAAGCT CGAGCTCTGG ACGCCTTGAT CCCTCCCACA TACGAATCAC

51 ACGCCTATCA CATTGCTGAC CTGCTTGAGC GTAGCTATTT GCCTCGCTAC
 51 TGCGGATAGT GTAACGACTG GACGAACTCG CATCGATAAA CGGAGCGATG

101 GGGTGAGGCT ACGAGCGGGT CCTCCGCATC TATCAGCTTA GGGCAGGGCT
101 CCCACTCCGA TGCTCGCCCA GGAGGCGTAG ATAGTCGAAT CCCGTCCCGA

151 CTATTATGCC GGGTGAGGTG GAGCTGAGCG GTGTGCCTAT CATGAGTGAG
151 GATAATACGG CCCACTCCAC CTCGACTCGC CACACGGATA GTACTCACTC

201 GAGCGGTGCT CTAAGCTGCG CACTAAGAAG GAGCTGCGAA TGGGCGGAAG
201 CTCGCCACGA GATTCGACGC GTGATTCTTC CTCGACGCTT ACCCGCCTTC

251 AAGCGGTGTG CCGCCTAGAT AGCCAACTAC GGGGCTGCCC AGCTGCACTA
251 TTCGCCACAC GGCGGATCTA TCGGTTGATG CCCCGACGCG TCGACGTGAT

301 TGACCTAGGG TGGGCGGTCC TCTATCAAGC TGCGCAGCGA GCCTAGCCAG
301 ACTGGATCCC ACCCGCCAGG AGATAGTTCG ACGCGTCGCT CGGATCGGTC

351 CTGAGCGGTG TGCAGCCCGC TAGTTAGCAA AGTGAGGAGC TGAGTGAGGC
351 GACTCGCCAC ACGTCGGGCG ATCAATCGTT TCACTCCTCG ACTCACTCCG

401 CGGCTGAAAC GCTAGTTAGC AAAGTGAGGA GCTGAGTGAG GCATCTATTT
401 GCCGACTTTG CGATCAATCG TTTCACTCCT CGACTCACTC CGTAGATAAA

451 GCGAGGGCTT AGTGAGCTGC ACTAACAGCT GAAGCTAGCA GGTAGCCTCT
451 CGCTCCCGAA TCACTCGACG TGATTGTCGA CTTCGATCGT CCATCGGAGA

501 ACAGCTATTT GCTCAAGCTC CGGTGGGGTG GGCTTGCTGA CTAGGGAGGG
501 TGTCGATAAA CGAGTTCGAG GCCACCCCAC CCGAACGACT GATCCCTCCC

551 TGGGTAGGAG CTGGCTTATG CAAGCTTGGC GT    (SEQ ID NO:1)
551 ACCCATCCTC GACCGAATAC GTTCGAACCG CA    (SEQ ID NO:2)
```

FIG. 5A

DNA_Encrypted_F1 (160 bp)(SEQ ID NO:3)
```
  1 GTGAATTCGA GCTCGAGACC TGCGGAACTA GGGAGGGTGT ATGCTTAGTG
 51 ACGCCTATCA CATTGCTGAC CTGCTTGAGC GTAGCTATTT GCCTCGCTAC
101 GGGTGAGGCT ACGAGCGGGT CCTCCGCATC TATCAGCTTA GGGCAGGGCT
151 CTATTATGCC
```

DNA_Encrypted_F2 (140 bp)(SEQ ID NO:4)
```
  1 GGGTGAGGTG GAGCTGAGCG GTGTGCCTAT CATGAGTGAG GAGCGGTGCT
 51 CTAAGCTGCG CACTAAGAAG GAGCTGCGAA TGGGCGGAAG AAGCGGTGTG
101 CCGCCTAGAT AGCGAACTAC GGGGCTGCGC AGCTGCACTA
```

DNA_Encrypted_F3 (150 bp)(SEQ ID NO:5)
```
  1 TGACCTAGGG TGGGCGGTCC TCTATCAAGC TGCGCAGCGA GCCTAGCCAG
 51 CTGAGCGGTG TGCAGCCCGC TAGTTAGCAA AGTGAGGAGC TGAGTGAGGG
101 CGGCTGAAAC GCTAGTTAGC AAAGTGAGGA GCTGAGTGAG GCATCTATTT
```

DNA_Encrypted_F4 (117 bp)(SEQ ID NO:6)
```
  1 GCGAGGGCTT AGTGAGCTGC ACTAACAGCT GAAGCTAGCA GGTAGCCTCT
 51 ACAGCTATTT GCTCAAGCTC CGGTGGGGTG GGCTTGCTGA CTAGGGAGGG
101 TGGGTAGGAG CTGGCTT
```

DNA_Encrypted_R1 (151 bp)(SEQ ID NO:7)
```
  1 TCACCCGGCA TAATAGAGCC CTGCCCTAAG CTGATAGATG CGGAGGACCC
 51 GCTCGTAGCC TCACCCGTAG CGAGGCAAAT AGCTACGCTC AAGCAGGTCA
101 GCAATGTGAT AGGCGTCACT AAGCATACAC CCTCCCTAGT TCCGCAGGTC
151 T
```

DNA_Encrypted_R2 (140 bp)(SEQ ID NO:8)
```
  1 AGGTCATAGT GCAGCTGCGC AGCCCCGTAG TTCGCTATCT AGGCGGCACA
 51 CCGCTTCTTC CGCCCATTCG CAGCTCCTTC TTAGTGCGCA GCTTAGAGCA
101 CCGCTCCTCA CTCATGATAG GCACACCGCT CAGCTCCACC
```

DNA_Encrypted_R3 (150 bp)(SEQ ID NO:9)
```
  1 CCTCGCAAAT AGATGCCTCA CTCAGCTCCT CACTTTGCTA ACTAGCGTTT
 51 CAGCCGCCCT CACTCAGCTC CTCACTTTGC TAACTAGCGG GCTGCACACC
101 GCTCAGCTGG CTAGGCTCGC TGCGCAGCTT GATAGAGGAC CGCCCACCCT
```

DNA_Encrypted_R4 (126 bp)(SEQ ID NO:10)
```
  1 ACGCCAAGCT TGCATAAGCC AGCTCCTACC CACCCTCCCT AGTCAGCAAG
 51 CCCACCCCAC CGGAGCTTGA GCAAATAGCT GTAGAGGCTA CCTGCTAGCT
101 TCAGCTGTTA GTGCAGCTCA CTAAGC
```

FIG. 5B

Frequencing of Correct Characters in a Message (%)

Plaintext message
This project, Synthetic DNA for Highly Secure Information Storage and Transmission, was funded through Sandia National Laboratories' Laboratory Directed Research & Development program.

FIG. 7B

20% correct (Space and a/A)
QZA@ KYjT!nfl rDJfZ!fAn yhb EjY UASZOD r!nzY! GJEjYiafAjJ rfjYaS! aJ: QYaJ@iA@@AjJl ca@ EzJ:!: fZYjzSZ raJ:Aa hafAjJaO xaRjYafjYA!@? xaRjYafjYD yAY!nf!: e!@!aYnZ m y!H!OjKi!Jf KYjSYaik

FIG. 7C

19% correct (Space and o/O)
B:KG aSO?&xj@ kiqj:&jKx z.D WOS "Ko:,i k&xdS& JqWOS;NjKOq kjOSNo& Nqb BSNqG;KGGKOq@ VNG Wdqb&b j:SOdo: kNqbKN .NjKOqN, wNUOSNjOSK&Gt wNUOSNjOSi zKS&xj&b c&G&NSx: u z&Z&,Oa;&qj aSOoSN;f

FIG. 7D

17% correct (Space and i/I)
fdlr KGita?Nu hRMNdaNI? ,.k piG 'I&dHR ha?eGa qMpiGw@NIiM hNiG@&a @MF fG@MrwIrrliMu P@r peMFaF NdGie&d h@MFI@ .@NIiM@H y@XiG@NiGlar! y@XiG@NiGR ,IGa?NaF sara@G?d b ,a:aHiKwaMN KGi&G@wT

FIG. 7E

Dear Mr. Wilson: I am informed that the Atomic Energy Commission intends to ask that the Bell Laboratories accept under contract the direction of Sandia Laboratory in Albuquerque, New Mexico. This operation, which is a vital segment of the atomic weapons program, is of extreme importance and urgency in the national defense, and should have the best possible technical direction. I hope that after you have heard more detail from the Atomic Energy Commission, your organization will find it possible to undertake the task. In my opinion you have here an opportunity to render an exceptional service in the national interest. I am writing a similar note direct to Dr. O. E. Buckley. Very sincerely yours, Harry Truman

FIG. 8A

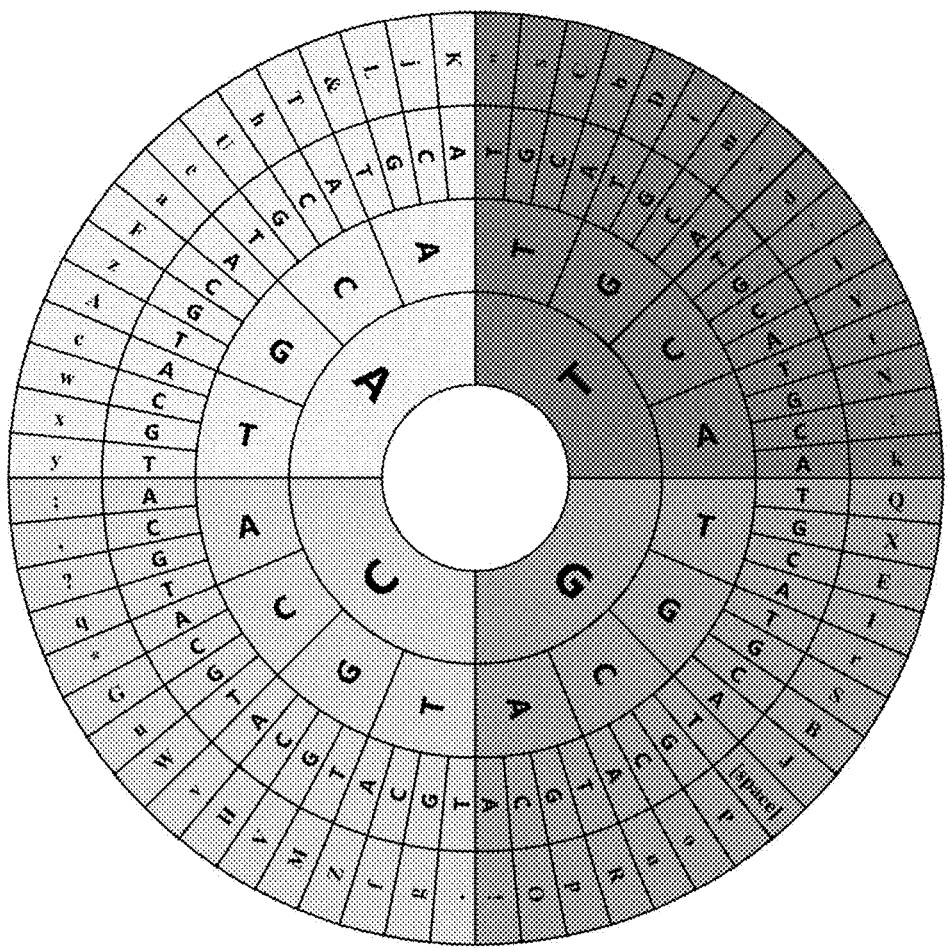

FIG. 8B

```
   1 TGTACTAGAG GTGCTCGTGG TCTTGCTCCT TGGTCCTTGG CCGCATACGC
  51 TGTAGCTAGA TGCGCTTGGG CACTCGCCGG TTGCACTTCT GCTTATACCA
 101 GATATGCTTA TACCACTGCT AGTTATGCCT GCTGGATAGC TGTCGCAACT
 151 GGTCTGATTG CTTTCGCCTG CTGCTGGTTG TTGTGGGCCG CAGCTTGGGC
 201 ATATACTGCA TCTTTGGCTT ATGCCGCTAG ATTGTAAGCT TATACCAGAT
 251 ATGCTTATAC CACTGCTGGC ACTTCCTCCG CTAAGAGATT AGCCGGTAGA
 301 TATGCCGGTT GGACTTTGGC TAGAATAATA ACTGAGTATG CTCCGGCATC
 351 TACTGGTGCT ATAGCCGCAT ATGGTAGAAT ATATGCTTAT ACCACTGCTT
 401 CTTGGGGTAC TATATATTGG GCCGCAGCTG CCCTCGCTGG GAGAGCATCT
 451 TGGAGAGCTA AGAGATTAGC CGGTAGATAT GCCGGTATTG CTTGGGCAGC
 501 TAGTTCCTTA CCGCATCCGA CTGGTCATCC GACTCACGCT TAGACTATCG
 551 CTCGTACTAT GTGGATAGCC CTTGCTACAA CCTGGTTGGC TGCCGAGACT
 601 GGTAGATATT GGGCCGCACA CGCTATCACC TGGATAACCG CTTGGTTGGC
 651 TAGAGCTCGA TGGTATAGAT CCGCTTTGAC TCTGTGCACT GCATATGCTG
 701 CCCTCGCTTA TACCACTGCT AGATATGCCT GCTGGATAGC TATCACTAGA
 751 GAGGCCGCAT TGGCTGAGGG TGCCCTGGGT AGATGCCACG CTTGGTTGGC
 801 TGCCCTCGCT ACTATGTATG GTACTTGCAC TGCTTGGTGC GAGGCCGGTT
 851 ATAGAGCAAT AACTGCTAGA GCATCTGCTC CGGGTCTGAC TGCAATAATT
 901 GCTTGGGCAG CTTATACCAC TGCTGCAAGA TATTGGGCCG CAAGATCCGC
 951 TTCTACTCTC ACTGCATTGA CTCACGCTAG AGCATCTGCT TTGACCGCCC
1001 CGTCCTCTGC TACCAGACGA ACTGCTTATA CCACTGCTTT AACTTTGTAT
1051 GCTGAGGCCT TGTTGTGGTT ATCCACTGCT TATACTATAA CCGCATGGAT
1101 AAGATCCGCT TCTTGGGGTA CTATATATTG GGCCGCACTT GCTGTAGCTA
1151 CCGCCGAGAC TGCTTATACC AGATATGCTA GACTCTATAC TGGTGCTATT
1201 GCCCCGGCTA CCAGACGAAC TGCTACCACT AGAGGTTCTG CTTGCGCCGG
1251 TACTGCTTCT ACTTATAGAT GGTCCGCTCT CGGTGCCTGC GCTTATACCA
1301 CTGCTAGTTA TGCCTGCTGG ATAGCTGTCG CAACTGGTCT GATTGCTTTC
1351 GCCTGCTGCT GGTTGTTGTG GCCGCACAC GCTATTGCCC CGGGTGCTGC
1401 CGGTCTGAGA GCATGGAGGA GATATTGGGC CGCAGCTATC TGGTCCTCCG
1451 CTCTCTGGGC ATCTGCTTGG TATGCTGAGG CCTTGTTGTG GTTATCCACT
1501 GCTTATGCCG CTCCGGCATC TACTGGTTAT AGATAAACTG CTTATACCAC
1551 TGCTTATAGA TTGTAACTTG CTGTAGCAGC TTGCATTGCT GCCGAGTGGG
1601 CATGGGCCGC AGCTATTGCC CCGGCTACCA GACGAACTGC TACCACTGGT
1651 ACTGCTAGAG CAGCTGCCGA GGAGGCCGGT TATCCGGCAT GGTATATTGC
1701 TTATGCCGCT GGTACTGCAT CTACTGGTGC TAGAGCAGCT ACTATGATAA
1751 CTGAGTATTG GGCCGCAAGA TCCGCTTTGA CTGGTCGATG GATAACTGCT
1801 TGGGCAGCTT ATACCACTGC TGCAAGATAT TGGGCCGCAA GATCCGCTTG
1851 GGCATATACT GGTACTTTGT ATCTTGCTGT AGCTAGATGC GCTATCGGTT
1901 GGTATTGGGC ACTGGCTAGA GCTTTGTGGT GCTGGTCCAG AGGTGCTGCA
1951 GCCTATACTG CTTCTTGGGG TACTATATAT GCTTATGCCG CTTGTGGTCT
2001 TGCTGACCTT GCTGTCCTTG CTGGCCCGAT ATAATCCACT ATTCTTGCTC
2051 GGACTGGTAT TGCTTTGTGG GCAATAACTG GTACTTCCAT TGCTATTGCC
2101 CCGGGTTTGC ACGCTCGCAG AGGTGGTATT GCTACAGGTC CGTGCAGAGC
2151 A                                           (SEQ ID NO: 11)
```

FIG. 8C

I have a dream that my four little children will one day live in a nation where they will not be judged by the color of their skin but by the content of their character. I have a dream today! I have a dream that one day, down in Alabama, with its vicious racists, with its governor having his lips dripping with the words of "interposition" and "nullification" -- one day right there in Alabama little black boys and black girls will be able to join hands with little white boys and white girls as sisters and brothers. I have a dream today! I have a dream that one day every valley shall be exalted, and every hill and mountain shall be made low, the rough places will be made plain, and the crooked places will be made straight; "and the glory of the Lord shall be revealed and all flesh shall see it together." This is our hope, and this is the faith that I go back to the South with. With this faith, we will be able to hew out of the mountain of despair a stone of hope. With this faith, we will be able to transform the jangling discords of our nation into a beautiful symphony of brotherhood. With this faith, we will be able to work together, to pray together, to struggle together, to go to jail together, to stand up for freedom together, knowing that we will be free one day. And if America is to be a great nation, this must become true. And so let freedom ring from the prodigious hilltops of New Hampshire. Let freedom ring from the mighty mountains of New York. Let freedom ring from the heightening Alleghenies of Pennsylvania. Let freedom ring from the snow-capped Rockies of Colorado. Let freedom ring from the curvaceous slopes of California. But not only that: Let freedom ring from Stone Mountain of Georgia. Let freedom ring from Lookout Mountain of Tennessee. Let freedom ring from every hill and molehill of Mississippi. From every mountainside, let freedom ring. And when this happens, and when we allow freedom ring, when we let it ring from every village and every hamlet, from every state and every city, we will be able to speed up that day when all of God's children, black men and white men, Jews and Gentiles, Protestants and Catholics, will be able to join hands and sing in the words of the old Negro spiritual: Free at last! Free at last! Thank God Almighty, we are free at last!

FIG. 9A

```
   1 GATTTGCTGG CGCTTTAGTA CGACTCGGTC TATAGTCATA TAAGTCAGCT
  51 GATACTAACT GGGTAAAGTC TGTAACCGGG TTTCGGGGGT CGATAGGCAT
 101 CCCCCCTAGA CCAAGAGAAG AACCATTAAC AGTTACGTAA ATGGGATGAC
 151 AATGGCCGGC CTCGTCGACA TGCCTGCCTT GGACCTGCAG GGGTACTCAC
 201 TAAATTTATG ATTTGGGGAA CCTCCTGGAT GACTAGAGAG TCCACTCCGC
 251 TTGCGAGCCT GCAGCGTGAC TTAGTCGAGT AGGCTAGACT ACTTCCCATT
 301 TCATAACATT AGTTATGTGA ACATGGCAAT ACGGGCGAGA GCGTACGATC
 351 TCACCCGCGG CAGCGCTCAC GGACTCGTGT AATTACTAGG AGCGTAAGCT
 401 GCTGTGGAGA GCCTCAATCC CTTAGTATTA CAATTCGAGG ACCTGAATCC
 451 AGAAGCCTCT CGAGTATCCC ATATTGGCCA GGCTTACGCA GGCTATACGC
 501 TAGGAGCACC AAACACTGTT CAATGGTGCA AATATGCCCG GGCCGTTCCG
 551 TTCGTCAGTG TCGCGATAAT ATTGACCCGC ATCGTTAACT AAATTTCTTC
 601 AGCGCAGACG CATTGACACT CGCGTGCGAC TGTATATTGC GTGCGTGGGT
 651 AGAAACCATC CAACCGACAG TTTCGTGCTA CCGTCGGTTA CCACCAGACA
 701 TCAGCGCTGA ACCGATAGCC GCGCTTACAG AAATGCTTCG CGAATGAACT
 751 TGACCGGACT TATTTCCGAA TATGCTGGCG ATAATCAATC GATCGGCTGT
 801 TAGTCGCCCC GGTTTAGTCT TCCCAACTGG GTAAAGCACG TAACCGGGGC
 851 CCTAATTCCA GTCGAAATGT TGGGGGCAAG GACCCATATG TGTGGGCCCA
 901 GTAACCACTA GCCCTGCTTT AACGTCTAGA TCCTGATACT TCTGCAAGGT
 951 ACCCCTCGGA AACCGATGTG ATTTCTATTA TGCACTGGAT CTAAGGGTCA
1001 GTTTGCATCC CCGGTACTCC TAAGGGAAAT GGATGTAATG GAGTGAAACA
1051 AGGCCTAGGA GATTACATTC ATCGTGGAAG ACGGCACATT CCTCTTTCAC
1101 AGTAAACACC TATGAGTAGA CTCGGTGAGG CAGCAGAGAG ACAACATGAG
1151 ATGAGAATTC GGACGGTTGC GGGGTCCTAG TGTAAGCAAC TCCGGCTTAG
1201 GCTTTGTATG TAAGGCTAAA GTCCACTACC TTACGATACA TACGCTCAGG
1251 CTAGTGTTAT GTATCATTGC TCCGAGTTGG TGCAACCTCC AGATCATATC
1301 TGGTCTATGC GATATGATAC ACGCTGTACT CTGGTAACAC CGTCTGCGCC
1351 ATACTTTGGT GCCAAGTCCT ACAGCTTAGG TGGTCAGCCG TAAAGAACAG
1401 CCGTATAGAA TAGAATGTGG ATCGCCACTG ACTGTTTGGT CAATACGTAC
1451 GTCCCGAGCG CCGCAATTCG TTGAGCAAAC CCTCGATAAC TGCGGAGCTG
1501 CACTATTTCT TCTTGAGTGC TGGAGTAGGA GGCGCATTCT CTAATATAAC
1551 CATGGCGAAC AATCAGAATT TCACCGGCTA CTGCAAGGCA ACCGAAAGGG
1601 CAGGCGGTGT GTATGAATAA ATATCCAACG CTATCCTGAA GGGCAATGCG
1651 ATCTGTTAAT AGCCTTCGGG TGTCTCGTCT TTGCCCAATC CGTCTTGTTT
1701 AGTTACCCGA AATGCTGCGT ATGTAAGCAA CGTCGGGGCC TCGCTAGTCA
1751 CGGATCGGTC TTAAAACTGG GTGCCCCGGG GGAGTGTGGA TTCCCAGTCG
1801 TACCGTTGTA GCCTTGCACA                    (SEQ ID NO:12)
```

FIG. 9B

| Text | DNA-1 | DNA-2 | DNA-3 | DNA-4 | DNA-5 | DNA-6 | DNA-7 | DNA-8 | DNA-9 | DNA-10 | DNA-11 |
|---|---|---|---|---|---|---|---|---|---|---|---|
| [space] | TGCT | TCGG | TAGT | AACT | CGGG | GTCG | GACC | GTAA | CCTG | GTAC | TGAT |
| ! | TATT | | | | | | | | | | |
| " | TGGT | | | | | | | | | | |
| & | CCGA | | | | | | | | | | |
| ( | GCAA | | | | | | | | | | |
| ) | TGCC | | | | | | | | | | |
| , | CAAG | | | | | | | | | | |
| . | ACGT | | | | | | | | | | |
| ' | TCGT | | | | | | | | | | |
| 0 | AAGT | | | | | | | | | | |
| 1 | AAAA | | | | | | | | | | |
| 2 | TTTG | | | | | | | | | | |
| 3 | AGAC | | | | | | | | | | |
| 4 | GGAT | | | | | | | | | | |
| 5 | TTTT | | | | | | | | | | |
| 6 | GGGA | | | | | | | | | | |
| 7 | AGGT | | | | | | | | | | |
| 8 | CAGT | | | | | | | | | | |
| 9 | GTTA | | | | | | | | | | |
| : | TTCA | | | | | | | | | | |
| ; | GACG | | | | | | | | | | |
| ? | TCCT | | | | | | | | | | |
| @ | TGTC | | | | | | | | | | |
| a | CTTT | TCTA | CTGA | TCTG | GGAA | GCAG | AGTC | GTGG | AAAC | ACCA | GAAC |
| b | GTGT | ATCC | GGTG | GGCC | GATC | AATC | | | | | |
| c | ATGG | GAAT | ATAT | TTGC | CATC | GTCA | | | | | |
| d | CATA | CGGC | TTGG | AGCT | GAGC | AGCC | CTTG | CGCC | AAAT | | |
| e | CGAC | TCAG | TTAC | TCGA | TTTA | TCCA | AACA | TTAT | ATAC | AATT | TGGA |
| f | ATAG | ATTG | CAGA | ATCA | | | | | | | |
| g | GCTG | TCTT | AGAT | GTCC | | | | | | | |
| h | GGCG | AAAG | GATG | TCAT | GGCA | ATTC | TACG | AGTG | CACT | GTGC | TACC |
| i | GATT | GAAG | ACAA | GGAC | CTAG | GCTT | AGGC | ACGA | CTAT | ACAC | TGCG |
| j | GGAG | | | | | | | | | | |
| k | CCAA | | | | | | | | | | |
| l | AAGA | ACAG | TGGC | CTGC | AGGG | ATGA | TCTC | ACCC | AAGC | AACG | GGTC |
| m | TACT | TTTC | ATGC | TCCC | | | | | | | |
| n | CATG | TAAA | GCGA | ACTT | CTAC | CAGC | TGTT | CCGC | CTAA | TAAT | CCCA |
| o | GCAT | TCAC | TAGA | GCTC | CCAG | CTCT | CCAT | TGAC | AGCG | TGAA | GCCC |
| p | TGTA | | | | | | | | | | |
| q | TTGT | | | | | | | | | | |
| r | TAAG | CCTA | CTCG | TTAG | GGAG | ACGC | ACTG | GTAG | AGTT | GCGC | CCGG |
| s | AGCA | TGCA | GGTA | AATG | GAAA | CACA | GGTT | | | | |
| t | GGGT | TAAC | AACC | ATTA | GAGT | ACAT | ACGG | TACA | GGCT | TATG | CGTC |
| u | CCCC | CGTA | CAAA | | | | | | | | |
| v | AGTA | AGAG | GACA | TCAA | ATCT | | | | | | |
| w | TCTT | CATT | GCGT | TGGG | CCCT | AGGA | | | | | |
| x | GCCG | | | | | | | | | | |
| y | GGGG | CCTC | GGGC | CTTA | GTTC | GACT | | | | | |
| z | CACC | | | | | | | | | | |

FIG. 9C

… # SYNTHETIC NUCLEIC ACIDS FOR INFORMATION STORAGE AND TRANSMISSION

CROSS-REFERENCE TO RELATED APPLICATION

This application claims the benefit of U.S. Provisional Application No. 62/711,964, filed Jul. 30, 2018, which is hereby incorporated by reference in its entirety.

REFERENCE TO A COMPUTER PROGRAM LISTING APPENDIX

A computer program listing appendix including an ASCII formatted file accompanies this application. The appendix includes a file named "SD14068_ST25.txt," created on Jul. 15, 2019 (size of 10.2 kilobytes), which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to method for storing and transmitting information by employing a nucleic acid construct. The nucleic acid construct can include a lock region; a translation key region that corresponds to the identity of a key; and a message region including a nucleic sequence that corresponds to an encrypted message.

BACKGROUND OF THE INVENTION

Protection and maintenance of information remains a challenging issue. Digital storage and transmission have proven increasingly susceptible to compromise. Nucleic acid (e.g., DNA) has been discussed as a medium for information storage, but limitations remain, such as providing effective encryption and decryption methodologies for secure information storage and retrieval.

SUMMARY OF THE INVENTION

The present invention relates, in part, to methods for securely translating and encrypting an information format (e.g., text and/or an image) into a nucleic acid construct. An exemplary construct includes synthetic DNA assemblies for safe and secure storage. In one non-limiting instance, the encryption method employs a key having each alphanumeric character and symbol in a text to be presented by a codon. For instance, by employing a triple codon (e.g., letter A is represented by codon AAA), the method permits the generation of more than $10^{89}$ unique libraries. Quadruplet codons may be used to increase the number of unique libraries of keys. Such libraries and keys can be modified, e.g., by minimizing highly repetitive nucleic acid regions. Lastly, the method can also enable decryption and translation of nucleic acid constructs back into the original information format.

In a first aspect, the present invention features a method for storing and transmitting information, the method including: converting each character in an information format into a triplet or quadruplet codon by employing a key, thereby generating an encrypted message represented by a plurality of nucleic acids or a complement thereof; synthesizing a nucleic acid construct including a lock region, a translation key region, and a message region; relaying the nucleic acid sequence of the lock region to a recipient and the key corresponding to the translation key region; and placing the nucleic acid construct on an object to be transmitted to the recipient.

In some embodiments, the lock region includes a primer binding region or a complement thereof, the translation key region includes a nucleic sequence that corresponds to the identity of the key or a complement thereof, and/or the message region having a nucleic sequence includes the encrypted message or a complement thereof.

In some embodiments, each character is one of an alphanumeric character, a symbol, a punctuation mark, and a space.

In some embodiments, the information format includes a text, an image, or a matrix.

In some embodiments, the key includes a different codon corresponding to a different character. In other embodiments, the codon includes three nucleic acids.

In some embodiments, the converting step includes: sectioning the information format into a plurality of sections; and converting each character in each section with a different key, wherein each key comprises a different codon corresponding to a different character.

In some embodiments, the translation key region includes a nucleic sequence that corresponds to the identity of each of the different keys.

In some embodiments, the converting step further includes: inserting one or more buffer regions in the encrypted message or a complement thereof. In particular embodiments, each buffer region includes a nucleic acid sequence that interrupts the information format, thereby generating a buffered, encrypted message represented by a plurality of nucleic acids.

In some embodiments, the lock region comprises of from about 15 to about 35 nucleic acids. In other embodiments, the translation key region comprises of from about 15 to about 35 nucleic acids.

In some embodiments, the nucleic acid construct includes a single-stranded sequence or a double-stranded sequence.

In some embodiments, the synthetizing step further includes: inserting a start codon indicating the beginning of the message region and inserting a stop codon indicating the end of the message region.

In some embodiments, the synthetizing step further includes: sectioning the nucleic acid construct, or a complement thereof, into a plurality of sections; and assembling each section by employing one or more of an exonuclease, a polymerase, and/or a ligase.

In other embodiments, the synthetizing step further includes: inserting the nucleic acid construct into a vector; and expressing the vector.

In yet other embodiments, the method further includes: degrading the nucleic acid construct by employing a nuclease.

In other embodiments, the method further includes: amplifying the nucleic acid construct by employing a polymerase, thereby generating a plurality of constructs.

In some embodiments, the method further includes: determining the nucleic acid sequence of at least one of the plurality of constructs.

In a second aspect, the present invention features a nucleic acid construct including: a lock region; a translation key region; and a message region, wherein the translation key region is disposed between the lock region and the message region.

In some embodiments, the lock region includes a first primer binding region or a complement thereof. In other embodiments, the translation key region includes a nucleic sequence that corresponds to the identity of a key or a complement thereof. In yet other embodiments, the message region includes a nucleic sequence that corresponds to an encrypted message, wherein the encrypted message comprises an information format having each character that is converted into a triplet or quadruplet codon by employing the key, or a complement thereof.

In some embodiments, the message region includes a buffered message region comprising a nucleic acid sequence that interrupts the information format.

In some embodiments, the construct further includes: a start region including a start codon, wherein the start region is in proximity to the 5' end of the message region; and a stop region including a stop codon, wherein the stop region is in proximity to the 3' end of the message region, wherein the key provides the identity of the start codon and the stop codon.

In some embodiments, the construct further includes: a first leader region including a second primer binding region, wherein the leader region is in proximity to the 5' end of the construct; an optional second leader region including a third primer binding region, wherein the second leader region is disposed between the translation key region and the message region; and a trailer region including a fourth primer binding region, wherein the trailer region is in proximity to the 3' end of the construct.

Additional details follow.

Definitions

As used herein, the term "about" means +/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1 taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

A sugar modification may include, but is not limited to, a locked nucleic acid (LNA, in which the 2'-hydroxyl is connected by a $C_{1-6}$ alkylene (e.g., a multivalent (e.g., bivalent, trivalent, tetravalent, etc.) form of an alkyl group) or $C_{1-6}$ heteroalkylene (e.g., a divalent form of an alkylene group containing one, two, three, or four non carbon heteroatoms (e.g., independently selected from the group consisting of nitrogen, oxygen, phosphorous, sulfur, or halo) bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. Exemplary modifications include modifications to the 2' position of a nucleic acid, such as 2'-O-methyl, 2'-halo (e.g., 2'-fluoro, 2'-chloro, etc.), 2'-alkyl (e.g., 2'-methyl, 2' ethyl, 2'-propyl, 2'-allyl, etc.), 2'-aryl (e.g., 2'-phenyl), 2'-alkaryl (e.g., 2'-benzyl), 2'-amino (e.g., 2'-NH$_2$, 2'-NR$^{N1}$R$^{N2}$, which each of R$^{N1}$ and R$^{N2}$ is, independently, H, alkyl, or alkaryl), 2'-alkoxy (e.g. 2'-O-methoxy, 2'-O-ethoxy, etc.), 2'-alkylamine (e.g., 2'-O-methylamine, 2'-O-ethylamine, etc.), 2'-O-alkylamine (e.g., 2'-O-methylamine, 2'-O-ethylamine, etc.), 2'-azido, 2'-O-cyanoalkyl (e.g., 2'-O-cyanomethyl), 2'-O-alkoxylalkyl (e.g., 2'-O-(2-methoxyethyl)), etc.

A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

By "salt" is meant an ionic form of a compound or structure (e.g., any formulas, sequences, compounds, or compositions described herein), which includes a cation or anion compound to form an electrically neutral compound or structure. Salts are well known in the art. For example, non-toxic salts, pharmaceutically acceptable salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter, "Overview of principles of hybridization and the strategy of nucleic acid probe assay," Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary, according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamic acid and aspartic acid; and a group of amino acids having sulfur containing side chains consists of cysteine and methionine. Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, WI, 53705). Such software may match similar sequences by assigning degrees of homology to various substitutions, deletions, and other modifications.

"Recombinant," as used herein, means that a particular nucleic acid, as defined herein, is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., DNA-targeting RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

By "linker" is meant any useful multivalent (e.g., bivalent) component useful for joining to different portions or segments. Exemplary linkers include a nucleic acid sequence, a chemical linker, etc. In one instance, the linker of the guiding component (e.g., linker L in the interacting portion of the guiding component) can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single-molecule guiding component is 4 nt.

The terms "nucleic acid regulatory sequences," "control elements," and "regulatory elements," used interchangeably herein, refer to transcriptional and translational control sequences, such as promoters, enhancers, polyadenylation signals, internal ribosomal entry sites (IRES), terminators, protein degradation signals, and the like, that provide for and/or regulate transcription of a sequence.

A "promoter sequence" is a nucleic acid regulatory region capable of binding nucleic acid polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a nucleic acid sequence that controls and regulates the transcription and translation of another nucleic acid sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

By "micro" is meant having at least one dimension that is less than 1 mm and, optionally, equal to or larger than about 1 µm. For instance, a microstructure (e.g., any structure described herein) can have a length, width, height, cross-sectional dimension, circumference, radius (e.g., external or internal radius), or diameter that is less than 1 mm.

By "nano" is meant having at least one dimension that is less than 1 µm but equal to or larger than about 1 nm. For instance, a nanostructure (e.g., any structure described herein, such as a nanoparticle) can have a length, width, height, cross-sectional dimension, circumference, radius (e.g., external or internal radius), or diameter that is less than 1 µm but equal to or larger than 1 nm. In other instances, the nanostructure has a dimension that is of from about 1 nm to about 1 µm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 4A-4B provides an exemplary synthetic DNA construct, dubbed "Test Message" (TM). The alphanumeric text was an acknowledgment to the LDRD program (FIG. 4A) and was encrypted into a nucleic acid sequence (SEQ ID NO:1) using a randomly generated translation key (FIG. 4B).

FIG. 5A-5B provides a double stranded sequence (SEQ ID NOs:1-2) including four forward (F1, F2, F3, and F4) and four reverse (R1, R2, R3, and R4) oligomers (SEQ ID NOs:3-10) that were designed from the encrypted sequence (TM) for insertion into the linear pUC19L vector.

FIG. 7A-7E shows the results for decryption of the TM with different keys. Provided is the frequency of correct characters in a message when using one of 100 random keys (FIG. 7A). Also provided is the input plaintext message (FIG. 7B) and three examples of output messages having either 20%, 19%, or 17% correct assignment of the codon to the input character when using a random key (FIG. 7C-7E)

FIG. 8A-8E shows results from another exemplary nucleic construct having an encrypted message. Provided is the "Truman Letter" (TL) message, in which the alphanumeric text (FIG. 8A) represents an excerpt from the letter written by President Truman in which he asked the head of AT&T to manage Sandia National Laboratories. The translation key (FIG. 8B) was used to encrypt and translation this letter into a 2,151-bp DNA sequence (FIG. 8C, SEQ ID NO:11) that was subdivided into four dsDNA fragments. These four fragments were assembled along with the pUC19L vector using the Gibson assembly method (FIG. 8D). Gel electrophoresis confirmed seven of twelve clones with the correct inserted DNA message (FIG. 8E).

FIG. 9A-9E shows construction of yet another nucleic construct having an encrypted message. Provided is an alphanumeric test message (DM) of the excerpt taken from Dr. Martin Luther King Jr.'s speech "I Have a Dream" (FIG. 9A). Also provided are a first fragment of the alphanumeric test message (FIG. 9A, highlighted text) and the corresponding encrypted message for that first fragment of the DM (SEQ ID NO:12, FIG. 9B), in which the translated DNA is sequenced based on a key shown in FIG. 9C (i.e., key for "DNA-1"). Also provided are the various translation keys generated to encrypt and translate the DM, in which multiple quadruplet codons were used to translate specific characters into DNA (FIG. 9C). Provided are plasmid construction of the DM (FIG. 9D) and gel electrophoresis of the plasmid following transformation into E. coli (FIG. 9E).

DETAILED DESCRIPTION OF THE INVENTION

Figure 1:
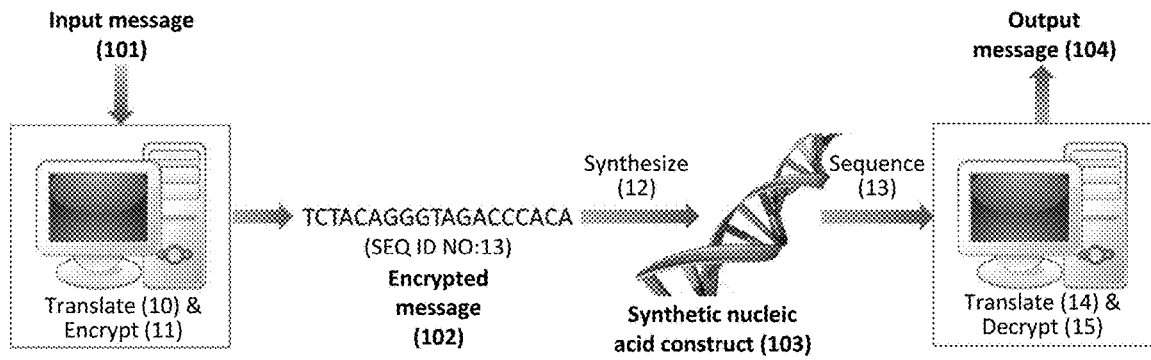
FIG. 1 provides a schematic of an exemplary method for storing and transmitting information.

The present invention relates to methods for storing and transmitting information, as well as nucleic constructs embodying encrypted messages. In particular embodiments, the method includes encrypting an information format by employing a key, thereby providing an encrypted message. The information format (e.g., input message, input, or message) can be any useful message, such as that provided in a text format (e.g., having a plurality of characters, including alphanumeric characters, symbols, punctuation marks, or spaces), an image, or a matrix (e.g., formed by assigning each pixel within an m×n image as a numerical value in a m×n matrix). The encrypted message can be a nucleic acid construct in any useful form (e.g., single stranded nucleic acid, double stranded nucleic acid, plasmid, or vector).

In one non-limiting instance, the method includes converting each character (or value, e.g., numerical value) in an information format into a codon (e.g., triplet or quadruplet codon) by employing a key, thereby generating an encrypted message represented by a plurality of nucleic acids. In some embodiments, the encrypted message can include a complement of a nucleic acid sequence provided by directly using the key. The key can include a plurality of codons, in which each codon corresponds to a character in the information format and each codon is represented by a plurality of nucleotides (e.g., three, four, or five nucleotides). In some embodiments, the key includes a different codon corresponding to a different character.

The input message can be divided into a plurality of sections, in which characters in each section can be converted by using a different key (e.g., where each key includes a different codon corresponding to a different character). Then, each encrypted message section can be combined into a continuous nucleic acid sequence, thereby providing the message region. Optionally, each encrypted message section can be associated with a translation key region indicating the key employed for that section. In one non-limiting embodiment, each translation key region is in proximity to the 5' end of each of the encrypted message section. In another non-limiting embodiment, the translation key region includes a nucleic sequence that corresponds to the identity of each key, and the message region includes a start region upstream of each encrypted message section and a stop region downstream of each encrypted message section.

The message region (encrypted message region) can include any other useful region upstream (towards the 5' end) or downstream (towards the 3' end) of the message region. Other useful regions include, e.g., a lock region (e.g., including a primer binding region, thereby identifying a sequence that could bind a primer sequence for nucleic acid translation and/or amplification), a translation key region (e.g., including a nucleic sequence that corresponds to the identity of a key, or a complement of the nucleic acid sequence), a leader region (e.g., including a primer binding region, thereby identifying a sequence that could bind a primer sequence for nucleic acid translation and/or amplification), a start region (e.g., including a nuclei acid sequence that indicates the beginning of the message region), a stop region (e.g., including a nuclei acid sequence that indicates the end of the message region), and/or a trailer region (e.g., including a primer binding region, thereby identifying a sequence that could bind a primer sequence for nucleic acid translation and/or amplification).

In some embodiments, the method can include synthesizing a nucleic acid construct (e.g., any described herein). The construct can include a message region having a nucleic sequence including the encrypted message or a complement thereof. Alternatively, the message region can include a plurality of message sections, in which each section includes a portion of the input message. In another embodiment, the message region can include one or more buffer regions (e.g., each buffer region including a nucleic acid sequence that interrupts the information format, thereby generating a buffered, encrypted message represented by a plurality of nucleic acids). The construct can include one or more lock regions in any useful location (e.g., in proximity to the 5' end of the construct, in proximity to the 5' end of the message region, or in proximity to the 5' end of each message section of the message region). The translation key region can include a nucleic sequence that corresponds to the identity of the key and/or each lock region (or a complement thereof).

Each of the regions within the construct can be of any useful length. In some embodiments, the message region includes of from about 500 to about 20,000 nucleic acids (e.g., base pairs). The lock region and/or translation key region can include, e.g., of from about 15 to nucleic acids. The start and/or stop regions can include, e.g., of from about 2 to 10 nucleic acids. The leader region and/or trailer region can include, e.g., of from about 2 to 35 nucleic acids.

Synthesis of the construct can include any other useful steps. Exemplary steps include, e.g., inserting a start region indicating the beginning of the message region, inserting a stop region indicating the end of the message region, sectioning the nucleic acid construct, or a complement thereof, into a plurality of sections, and/or assembling each section by employing one or more of an exonuclease, a polymerase, and/or a ligase. Yet further non-limiting steps can include inserting the nucleic acid construct into a vector, expressing the vector (e.g., within a cell), and/or providing a cell with the nucleic acid construct or a vector including the vector. Exemplary methods for nucleic acid synthesis include, e.g., array-based synthesis (e.g., employing photolabile nucleoside phosphoramidite chemistry on microarrays), column-based oligonucleotide synthesis (e.g., employing phosphoramidite-based oligo synthesis), polymerase cycling assembly (PCA)-based techniques, ligation-based techniques (e.g., employing ligase to join overlapping strands into longer fragments), Gibson assembly, circular polymerase extension cloning (CPEC), Golden Gate assembly, ligation cycling reaction, paper-clip assembly, sequence and ligation-independent cloning (SLIC), yeast assembly, etc., and combinations thereof (see, e.g., Leake D, "DNA synthesis steps up," *Genetic Engineering & Biotechnology News* 36(8), Aug. 15, 2016 (3 pp.); and Kosuri S et al., "Large-scale de novo DNA synthesis: technologies and applications," *Nat. Methods* 2014; 11:499-507).

The method can further include relaying information to the intended recipient of the nucleic acid construct. Exemplary information can include, e.g., a nucleic acid sequence of the lock region(s) and/or one or more keys corresponding to the translation key region(s). The method can also include providing the construct to the recipient (e.g., placing the nucleic acid construct on an object to be transmitted to the recipient).

The method can also include amplifying the nucleic acid construct (e.g., by employing a polymerase, thereby generating a plurality of constructs), isolating the nucleic acid construct (e.g., from a population of random nucleic acid sequences that do not include an encrypted message), determining the nucleic acid sequence (e.g., sequencing the construct), degrading the nucleic acid construct (e.g., by use of heat, chemical degradation, and/or enzymatic degradation), and/or translating the nucleic acid sequence into an interface providing an algorithm that employs a key, thereby providing a decrypted message. Exemplary methods for nucleic acid sequencing include, e.g., Sanger sequencing, next-generation sequencing (NGS, e.g., employing template immobilization, polymerase immobilization, emulsion-based amplification, solid-phase amplification, cyclic amplification and termination reactions, etc.), real time sequencing (e.g., employing a zero mode waveguide), sequencing by ligation (e.g., SOLiD sequencing), pyrosequencing, ion semiconductor sequence (e.g., Ion Torrent sequencing), nanopore sequencing, etc., and combinations thereof (see, e.g., Metzker M L, "Sequencing technologies—the next generation," *Nat. Rev. Genet.* 2010; 11:31-46). Such sequencing can be employed in combination with one or more techniques to amplify the nucleic acid construct, e.g., by use of polymerase chain reaction.

FIG. 1 provides an exemplary method for storing and transmitting information (e.g., an input message 101). The input message 101 can be provided to an algorithm (e.g., an executable code). During the translation step 10, the algorithm cycles through different codons, significantly reducing codon redundancy over long stretches of a nucleic acid sequence and increasing viability of synthesis. Upon finding an optimal key (e.g., that minimizes GC content, homopolymers, etc.), the input message is encrypted 11 with the identify key to provide an encrypted message 102 (SEQ ID NO:13) having a nucleic acid sequence in which each character of the input message is represented by one codon of the key (e.g., by converting each character in an information format into a triplet or quadruplet codon by employing a key, thereby generating an encrypted message). Then, the nucleic sequence designated to be the encrypted message is synthesized 12 as a nucleic acid construct 103. The construct can include any useful regions (e.g., any described herein). Upon receipt (and/or isolation) of the construct, the construct can be sequenced 13 to provide the nucleic acid sequence. Finally, the nucleic acid sequence can be translated 14 (e.g., by cycling through the algorithm and selecting the appropriate key) and decrypted 15 by replacing each codon with the corresponding character, thereby providing an output message 104.

Translation can include any useful process. In one non-limiting embodiment, translation can include randomly assigning a codon (e.g., a triplet nucleic acid) to a character (e.g., one or more of 64 letters, numbers, symbols, or nonsense) to build a key. The key can be selected to reduce characteristics that could be difficult to synthesize and/or to reduce coding redundancy, and the key can then be exported. Using the identified key, the input message can translated, thereby providing an encrypted message that can be exported.

The nucleic acid construct can be provided in any useful format. In one instance, the construct is provided as a spot (e.g., having a diameter of from about 10 μm to about 500 μm), a minimal volume (e.g., of from about 10 to about 1000 femtoliters). In yet other embodiments, the construct is provided in cold storage, room temperature storage, in liquid form, or in dried form (e.g., embedded in a material).

Nucleic Acid Construct

The present invention relates to a nucleic acid construct including an encrypted message (or a complement thereof). The construct can include other regions, including a lock region (e.g., including a first primer binding region or a complement thereof), a translation key region (e.g., including a nucleic sequence that corresponds to the identity of a key or a complement thereof), and a message region (e.g., including a nucleic sequence that corresponds to an encrypted message). As described herein, the encrypted message can include an information format having each character that is converted into a triplet or quadruplet codon by employing the key, thereby providing an encrypted nucleic acid sequence. The encrypted message can also include a complement of the encrypted nucleic acid sequence.

Figure 2A:
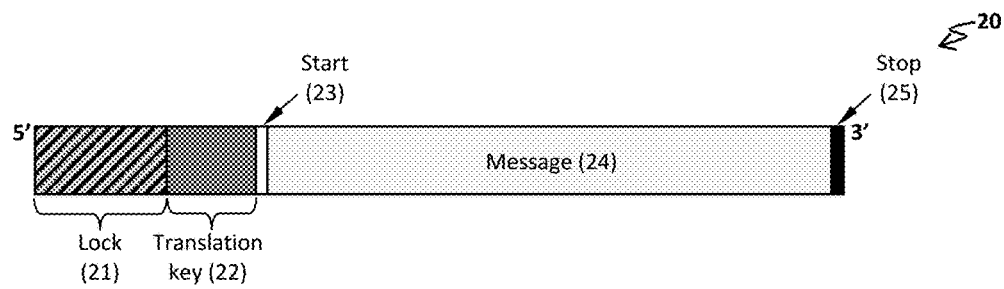
FIG. 2A-2D shows schematics of exemplary synthetic nucleic acid constructs. Provided is a nucleic acid construct 20 including a lock region 21, a translation key region 22, a start region 23, a message region 24, and a stop region 25 (FIG. 2A). Also provided are a further exemplary construct 200 including a buffered message region 204 (FIG. 2B), another exemplary construct 210 including a plurality of message sections 214A,214B (FIG. 2C), and yet another exemplary construct 220 including a plurality of message sections 224A,224B, in which each section includes a start region 223A,223B and a stop region 225A,225B (FIG. 2D).

In some embodiments, the nucleic acid construct 20 includes a lock region 21 (e.g., in proximity to the 5' end of the construct), a translation key region 22 (e.g., located between the lock region and the start region), a start region 23 (e.g., in proximity to the 5' end of the message region), a message region 24, and a stop region 25 (e.g., in proximity to the 3' end of the message region) (FIG. 2A).

Figure 2B:
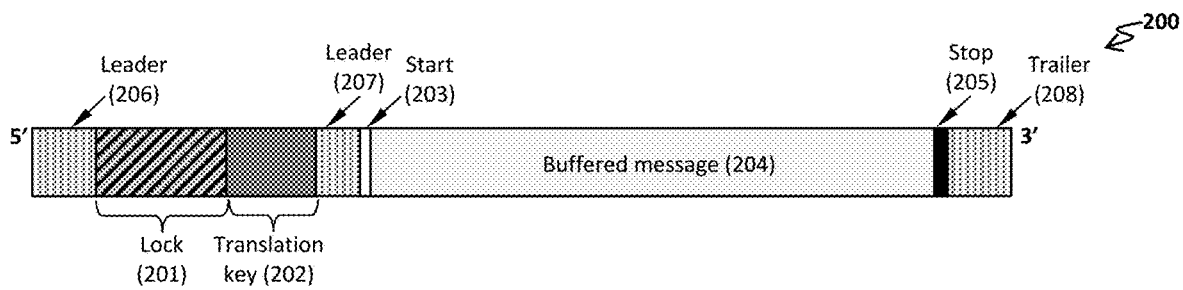
Figure 3:
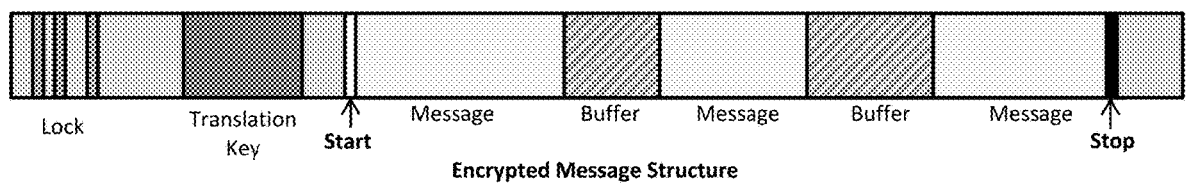
FIG. 3 shows a schematic of an exemplary synthetic nucleic acid construct that embodies an encrypted message structure.

The encrypted message can also be buffered, i.e., by including one or more buffered region. Each buffered region can include a nucleic acid sequence that interrupts the information format and can be located throughout the encrypted nucleic acid sequence. Exemplary buffered message regions are provided in FIG. 2B and FIG. 3. In some embodiments, the nucleic acid construct 200 includes a lock region 201 (e.g., in proximity to the 5' end of the construct), a translation key region 202 (e.g., located between the lock region and the start region), a start region 203 (e.g., in proximity to the 5' end of the message region), a buffered message region 204, and a stop region 205 (e.g., in proximity to the 3' end of the message region) (FIG. 2B). Another exemplary buffered region is provided in FIG. 3, in which two buffer regions are dispersed between three message sections, which together form the buffered message region.

A nucleic acid construct can further include one or more leader regions and/or trailer regions. Such regions can include, e.g., further primer binding regions that serve as locks, in which knowledge of the sequence of the primer binding region would facilitate sequencing and/or amplifying of the construct. In some embodiments, the nucleic acid construct 200 includes a first leader region 206 (e.g., in proximity to the 5' end of the construct), a second leader region 207 (e.g., in proximity to the 5' end of the message region), and a trailer region 208 (e.g., in proximity to the 3' end of the construct) (FIG. 2B).

The construct can have one or more start regions (e.g., start codons) and one or more stop regions (e.g., stop codons). In one embodiment, the start region is located in proximity to the 5' end of the message region, and the stop region is located in proximity to the 3' end of the message region. In another embodiment, the message region includes a plurality of message sections, a start region is located in proximity to the 5' end of each message section, and the stop region is located in proximity to the 3' end of each message section. In particular embodiments, the key provides the identity and/or location(s) of the start and stop codons.

Figure 2C:
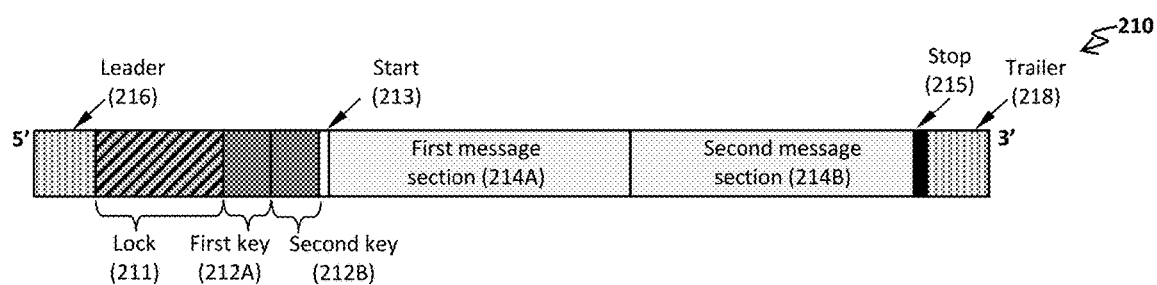

In some embodiments, the nucleic acid construct 210 includes an optional first leader region 216 (e.g., in proximity to the 5' end of the construct), a lock region 211 (e.g., in proximity to the 5' end of the construct), a first translation key region 212A (e.g., located between the lock region and the start region, where the first translation key region includes a nucleic acid sequence that corresponds to identifying a first key), a second translation key region 212B (e.g., located between the lock region and the start region, where the second translation key region includes a nucleic acid sequence that corresponds to identifying a second key), a start region 213 (e.g., in proximity to the 5' end of the message region), a message region including a first message section 214A encoded by the first key and a second message section 214B encoded by the second key, a stop region 215 (e.g., in proximity to the 3' end of the message region), and an optional trailer region 218 (e.g., in proximity to the 3' end of the construct) (FIG. 2C).

Figure 2D:
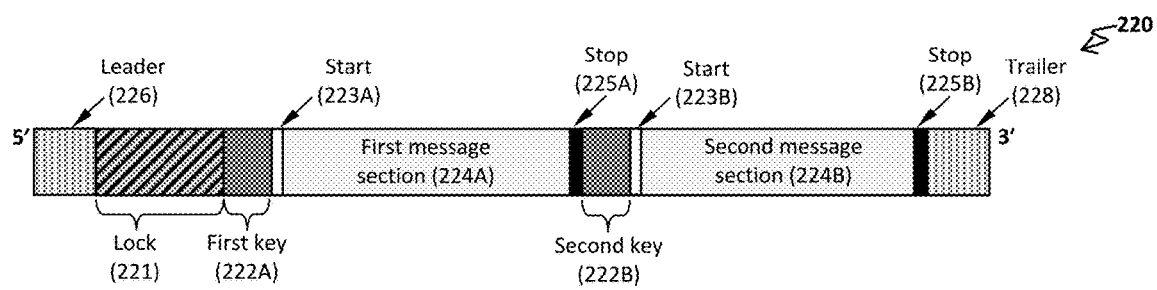

In other embodiments, the nucleic acid construct 220 includes an optional first leader region 226 (e.g., in proximity to the 5' end of the construct), a lock region 221 (e.g., in proximity to the 5' end of the construct), a first translation key region 222A (e.g., located between the lock region and the first start region, where the first translation key region includes a nucleic acid sequence that corresponds to identifying a first key), a first start region 223A (e.g., in proximity to the 5' end of the first message section), a first message section 224A encoded by the first key, a first stop region 225A (e.g., in proximity to the 3' end of the first message section), a second translation key region 222B (e.g., located between the first stop region and the second start region, where the second translation key region includes a nucleic acid sequence that corresponds to identifying a second key), a second start region 223B (e.g., in proximity to the 5' end of the message region), a second message section 224B encoded by the second key, a second stop region 225B (e.g., in proximity to the 3' end of the second message region), and an optional trailer region 228 (e.g., in proximity to the 3' end of the construct) (FIG. 2D).

The nucleic acid construct can provided in any useful manner. In one instance, the construct is provided as a plasmid, a vector, a double-stranded sequence, a single stranded sequence, or a packaged nucleic acid (e.g., employing a nanoparticle, a microparticle, a lipoplex, a liposome, a vesicle, a polymeric carrier, a histone, a cationic carrier, or a protein, such as a cationic protein).

EXAMPLES

Example 1: Synthetic DNA for Highly Secure Information Storage and Transmission

Protection of information remains a challenging issue. Digital storage and transmission, in particular, have proven increasingly susceptible to compromise, necessitating the development of disruptive technologies to secure highly sensitive information. DNA has been discussed as a medium for information storage, but limited by the speed and cost of both DNA synthesis and sequencing. Recent technology advances have enabled the development of prototype DNA systems for storing digital information. These proof-of-concept systems represent a paradigm for high-capacity, low maintenance information storage that also offers the ability to transmit information in a highly secure medium (e.g., DNA), as opposed to an encrypted digital format. Here, we have developed a method to apply the general premise of information storage in DNA and focused on developing a fundamentally novel approach for encrypting, translating, and storing encrypted text within DNA constructs.

In our approached, we employed codons (e.g., a triplet coding including three adjoining nucleotides or quadruplet codon including four adjoining nucleotides) to generate novel keys for encrypting messages. In one non-limiting instance, the design involved synthetic DNA constructs including the encrypted data itself and a "translation key," using sequences that specify the language for decoding the encrypted data. These functions were performed by a MAT-LAB® executable, EncrypDEMO, that we developed.

We have formalized a prototype executable, EncrypDEMO, in which text can be encrypted and translated into DNA language, and synthetic DNA constructs can be constructed to securely store and transmit this information. In particular, we converted three messages (including 184, 717, and 2,315 characters) into prototype DNA constructs encrypting these messages. The resulting constructs ranged in length from 552 to 9,240 DNA base pairs, which was designed using EncrypDEMO; and DNA constructs were successfully synthesized. Using one of these constructs, we demonstrated that DNA messages were recoverable after being spotted on a letter, and mailed across the country and back.

In addition to archiving historical documents, barcoding/watermarking synthetic materials (e.g., silicone foams) with synthetic DNA constructs was also explored. In particular, we embedded a DNA message in silicone rubber foam, stored these materials under ambient conditions, and demonstrated that the DNA message could be successfully recovered and read six months later. Lastly, we demonstrated the ability to recover and read DNA messages more than six months after being spotted on laboratory/office equipment (pipette, phone, computer mouse, etc.). Overall the work on this project has established a framework that can be widely applied for highly secure, information storage/transmission in a synthetic nanoscopic biomolecule, potentially transforming the future of information storage. Additional details follow.

Example 2: Exemplary Nucleic Acid Construct

We hypothesized that the nucleic acid construct can include various functional regions. In one non-limiting embodiment, the nucleic acid construct includes (i) a "lock" region securing the DNA from being "read" by anyone lacking authorization, (ii) a "translation key" region having a nucleic acid sequence that specifies the language for decoding the encrypted data, and (iii) the encrypted message itself composed of another nucleic acid sequence. In addition, this approach can allow the use of nonsense code sequences within the encrypted message (see, e.g., FIG. 3).

The nucleic acid construct can include a lock region. In one non-limiting embodiment, the message lock region includes a defined nucleic acid sequence (e.g., of from about 20 to 30 nucleotides) that permits sequencing of the encoded message (e.g., a primer binding region). The lock can serve as a two-factor authentication in that the receiver must possess both the proper primer sequence and the nucleic acid construct (e.g., by isolating the nucleic acid construct from a plurality of nonsense constructs that does not include the encrypted message). In the absence of the lock sequence and/or the primer sequence, a person trying to crack the code would need to try many different sequences (e.g., more than $10^{12}$ different primers) in order to sequence the message starting from the lock. The number of possible primers could be reduced by using shorter sequences and reconstructing the fragments in silico, but would require considerable laboratory and computational efforts.

In addition to the use of a lock for sequencing, independent locks could be placed at the 5' and 3' end of the sequence, enabling PCR amplification of the message. In this case, encrypted messages (or nucleic constructs including such messages) could be transmitted in amounts that are below what is needed to successfully sequence the message (particularly using a brute force, combinatorial approach). Thus, the receiver would need two primers (forward and reverse) to successfully amplify and sequence the message. Optimal length and location for the one or more lock sequences can be determined, e.g., by evaluating the level of security associated with locks and/or assessing potential mechanisms for subverting the lock and sequencing the data message.

The nucleic acid construct can include a translation key region. In one non-limiting embodiment, this region allows for the user to identify unique translation key associated with a specific library, thereby allowing for translation/decryption of the encoded message. In the absence of knowing how to translate the codons into alphanumeric text, the DNA sequence is merely a string of A, G, C, and T's with no meaning. For example, the AAA triplet codon could specify the letter "A" in one message, the number "5" in a different message, and a nonsense sequence in a third message. The translation key region can be inserted upstream of the encrypted message in the DNA construct, and when sequenced, provide information regarding what specific library is needed to decrypt the message. Exemplary methods for assigning a translation key to a given library include, e.g., assigning a static or dynamic translation key to libraries, identifying the number of characters for a secure translation key, and understanding how to distinguish the translation key from other non-functional DNA sequences.

The nucleic acid construct can include an encrypted message. In one non-limiting embodiment, correct translation of the encoded message requires that the message be read in the correct frame. In addition, the message may be encoded by either one of the two strands. If a triplet codon is used, then three nucleotides are assigned to each alphanumeric symbol and/or function (e.g., stop message, start message, etc.), as described above.

In certain embodiments, the encrypted message can include a start region (e.g., upstream of the encrypted message or in proximity to the 5' end of the encrypted message). For instance, one specific codon in the library can mark the beginning of a message (e.g., a start codon). In other non-limiting embodiments, the construct can include a stop region marking the end of the encrypted message (e.g., a stop codon located downstream of the encoded message or in proximity to the 3' end of the encrypted message).

Optionally, the encrypted message can include one or more buffer regions. In certain embodiments, a buffer region includes a nucleic acid sequence that does not correspond to the input message. Rather, the buffer region interrupts the message. In use, such buffer regions can be employed to confuse/mis-lead algorithms designed to crack the message code. With the proper translation key, these buffer regions can be recognized and clipped out, and the individual messages can be assembled to final form. Eukaryotic intron consensus sequences can be determined, such as dinucleotide GU at the 5' end (5'-GU), 5'-GUA, 5'-GTA, 5'-GTG, 5'-GT, 5'-AU, 5'-AT, 5'-AAGGTAAGT, 5'-AAGGTGAGT, 5'-CAGGTAAGT, 5'-CAGGTGAGT, or 5'-AGGT; or dinucleotide AG at the 3' end (AG-3'), TAG-3', UAG-3', CAG-3', CAGG-3', YAG-3', or AC-3'. Other modifications include evaluating buffer size, location, and frequency with regard to improvement in the level of security, as well as assessing the optimal set of nonsense characters necessary to avoid easy identification of buffers based on high codon redundancy.

Example 3: Encoding and Encrypting Messages

To date, the majority of methods for DNA-based storage involve translating DNA sequences into binary code. Our approach involved the translation of the message (e.g., including alphanumeric text and symbols) into DNA-based randomly generated codon translation keys. The universal genetic code used by living organisms includes 64 unique triplet codons formed from the four DNA bases, adenine (A), cytosine (C), guanine (G) and thymine (T). While the genetic code is degenerate (i.e., amino acids may be encoded by more than one DNA codon), our approach assigned a specific character (number, letter, punctuation, etc.) or function (stop, start, space) to each codon. In addition, codons may be assigned as "nonsense" for use in buffer regions.

Because a given character or function can be encoded by any of the 64 codons, the number of unique translation keys ($_nP_k$) can be determined as follows:

$$n!/(n-k)! \tag{1}$$

where n is the number of number of codons, and k is the number of objects (i.e., assigned characters or functions). Because n and k are equivalent in this case, the denominator simplifies to 1 (0!), and the number of unique libraries is equal to 64. Thus, brute force methods would require translating a given DNA message with ~$1.3 \times 10^{89}$ translation keys in order to successfully decrypt the message. By comparison, cracking 128-bit encryption requires trying ~$3.4 \times 10^{38}$ possible combinations to successfully decrypt the information. Transitioning to quadruplet codons would enable the assignment of 256 characters and virtually an infinite number of unique translation keys (256!). Thus, we believe that this codon-based approach will provide a robust means of encrypting information, and allows for future enhancement with regard to increasing security and the number of unique libraries.

We first focused efforts on developing a MATLAB® executable (called EncrypDEMO) capable of generating triplet codon translation keys for text encryption, and subsequently using the translation key to translate alphanumeric text. The initial version allowed the user to generate randomly generated translation keys of triplet codons that were assigned to lowercase and uppercase letters, numbers, and/or a set of common symbols. The translation key, or library, could be exported as an Excel file, and saved for future decryption of DNA messages. Once the translation key was generated, the user was able to enter an alphanumeric message and translate it into a synthetic DNA sequence, which could be exported as a text file. The executable also allowed the user to import both a translation key and DNA message file, and then decrypt the DNA sequence back into the original alphanumeric message.

The executable can also be adapted to include modifications that facilitate nucleic acid synthesis and/or enhance encryption. For instance, repeat occurrence of specific letters (e.g., e, n, a, t, etc.) and symbols (e.g., space) is present in the English language, which can create significant issues with DNA synthesis. For example, in a number of early tests, it was found that the "space" character represented up to 20% of the characters in a given alphanumeric message. As such the codon representing "space" appeared once in every five codons, on average, across the DNA sequence. DNA strands with highly repetitive strings of nucleotide bases, as well as palindromic sequences, can be challenging to synthesize. Thus, EncrypDEMO was specifically revised and tested with respect to enhance the probability of generating long DNA sequences that could be synthesized.

In one instance, a modification included allowing the user to select the use of triplet or quadruplet codons, allowing either 64 or 256 codons to be assigned to individual characters. As discussed above, this relatively minor change enables an essentially infinite number of translation keys (i.e., 256!) using quadruplet codons.

In another instance, a modification included the use of weighted and multiple assignment of codons (e.g., quadruplet codons) to the alphanumeric characters. For example, the executable was revised to first analyze the alphanumeric text, provide the frequency of each character in a given message, and employ the frequency data for weighted assignment of multiple triplet or quadruplet codons to the characters present in the message. For example, the "space" character is generally the most frequently encountered, and therefore could be randomly assigned 5-10 different quadruplet codons depending on the exact frequency of other characters in the message. During the translation step, the algorithm cycles through the different codons, significantly reducing codon redundancy over long stretches of DNA and increasing viability of synthesis. In one non-limiting embodiment, these modifications increased the percentage of sequencing passing the commercial synthesis algorithms for up to 2,000 base pair (bp) sequences (e.g., an increase of success from ~5% to over 80%).

Overall, we have developed a non-limiting embodiment of a software program that generates random DNA codon libraries for the encryption/decryption of text. The program allows the user to select from triple or quadruplet codons, and develops a unique library based on the text input. In some applications, our algorithm accounts for and mitigates repeat sequences in the message by using weighted codon assignments. The software also allows libraries to be exported, saved, and imported. Finally, the software permits the decryption and translation of DNA messages back to text.

Example 4: Exemplary Encrypted Constructs for Test Messages

We have taken three text documents and converted them to encrypted nucleic acid messages using our software: (1) LDRD acknowledgment, which was 184 text characters (552 bp DNA); (2) Truman letter asking Bell Labs to manage Sandia, which was 717 text characters (2,151 bp DNA); and (3) an excerpt of Martin Luther King Jr's "I Have a Dream" speech, which was 3,080 text characters (9,240 bp DNA). In all case, the nucleic acid messages were synthesized commercially and cloned into a plasmid vector. The plasmid (containing the message) was then transformed into E. coli for amplification. The plasmid DNA was re-isolated and sequencing of the DNA was performed. The resulting sequence data was imported into the software algorithm and decrypted. These proof-of-principles demonstrate the feasibility of the storing encrypted information in synthetic DNA. Additional details are provided in the following Examples.

Example 5: DNA Encrypted Construct—Test Message

Figure 4B:
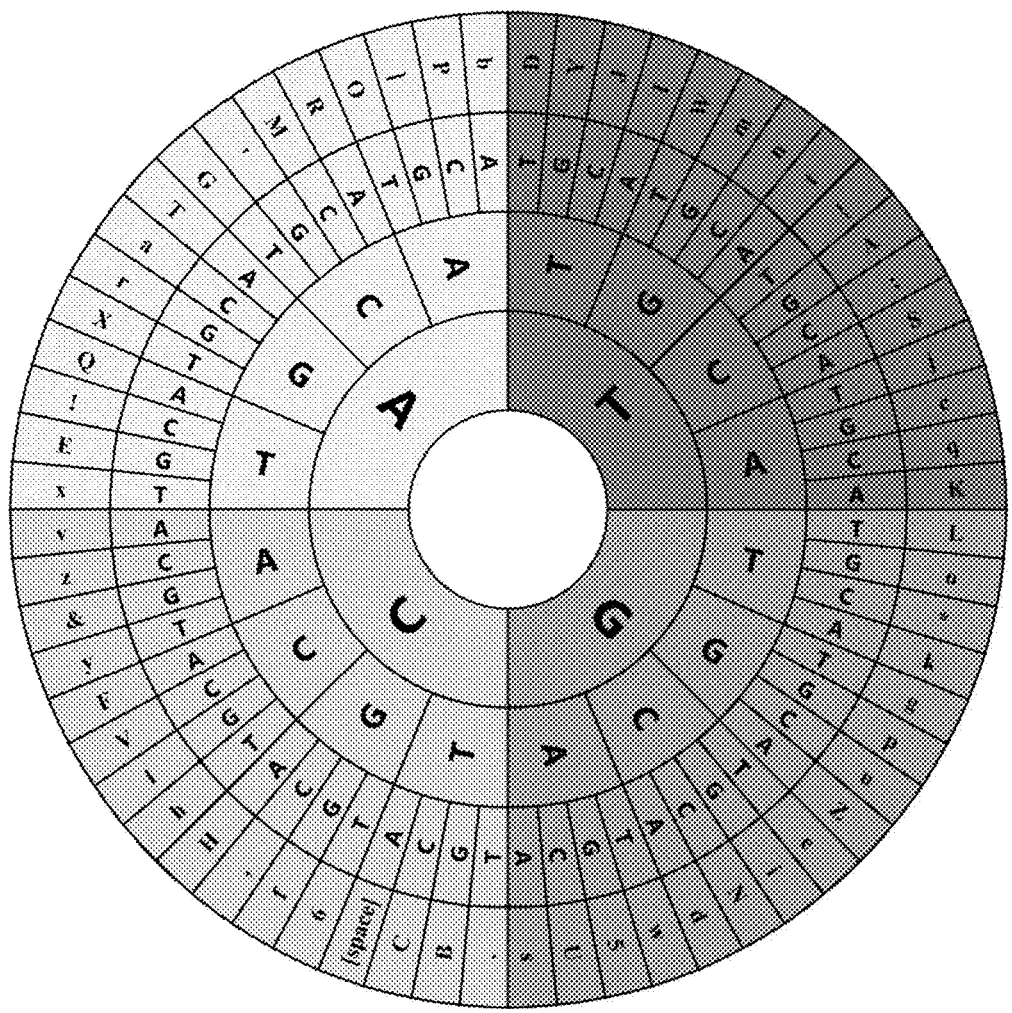

The initial DNA construct, called the Test Message (TM) was composed with the LDRD acknowledgment text: "This project, Synthetic DNA for Highly Secure Information Storage and Transmission, was funded through Sandia National Laboratories' Laboratory Directed Research & Development Program." (FIG. 4A). The text included 184 alphabetic characters, including punctuation and spacing. Using the EncrypDEMO and triplet codon encryption, a translation key was generated (FIG. 4B), and a 552-bp DNA sequence (SEQ ID NO:1, FIG. 4A) was created and passed initial screening with respect to synthesis.

The first approach for generating this DNA construct involved the synthesis of single-stranded DNA (ssDNA) oligomers, capable of being stitched together into a single DNA construct. Four forward (F1, F2, F3, and F4) and four reverse (R1, R2, R3, and R4) oligomers (FIG. 5A-5B) were designed from the encrypted sequence for insertion into the linear pUC19L vector. The individual oligomers ranged from 117 bp to 160 bp in size. Six bp and 15 bp homologous, overlapping ends for oligomer/oligomer and oligomer/vector annealing, respectively, were synthesized by Sigma-Aldrich.

For annealing, four reactions (F1 & R1, F2 & R2, F3 & R3, and F4 & R4) were prepared using 10 µL of each oligomer at an equimolar concentration of 27 µM. The reactions were placed in the thermocycler at 95° C. for 2 minutes, and ramp cooled to 25° C. over a 45-minute period of time. A second reaction was then prepared using 2.5 µL each of the four newly annealed double-stranded DNA. This reaction was placed in the thermocycler using the same conditions described above. The resulting DNA fragment (50 ng) was cloned into the pUC19L vector (100 ng) at a 2:1 insert:vector ratio. The cloning reaction was incubated at room temperature for 30 minutes with the GeneArt™ Seamless Cloning enzyme mix (Thermo Fisher Scientific Inc., Waltham, MA). The cloning reaction (8 µL) was immediately transformed into One Shot™ TOP10 competent cells (Thermo Fisher Scientific Inc.), and grown overnight at 37° C. on LB agar with ampicillin. Colonies were then selected and grown in liquid culture overnight at 37° C. Plasmids were isolated using Qiagen mini-prep plasmid kit (Qiagen NV, Hilden, Germany), digested with EcoRI and HindIII at 37° C. for 1 hour, and analyzed by DNA gel electrophoresis. No bands were detected on the gel, suggesting that the annealing reactions did not work. The annealing reactions were repeated with eight newly synthesized ssDNA oligomers from Integrated DNA Technologies, Inc. (IDT, Skokie, IL) with a 50-bp complimentary, overlapping 5' and 3' ends for cloning into pUC19L. No colonies were present after transformation, again suggesting that the annealing reaction failed.

Figure 6A:
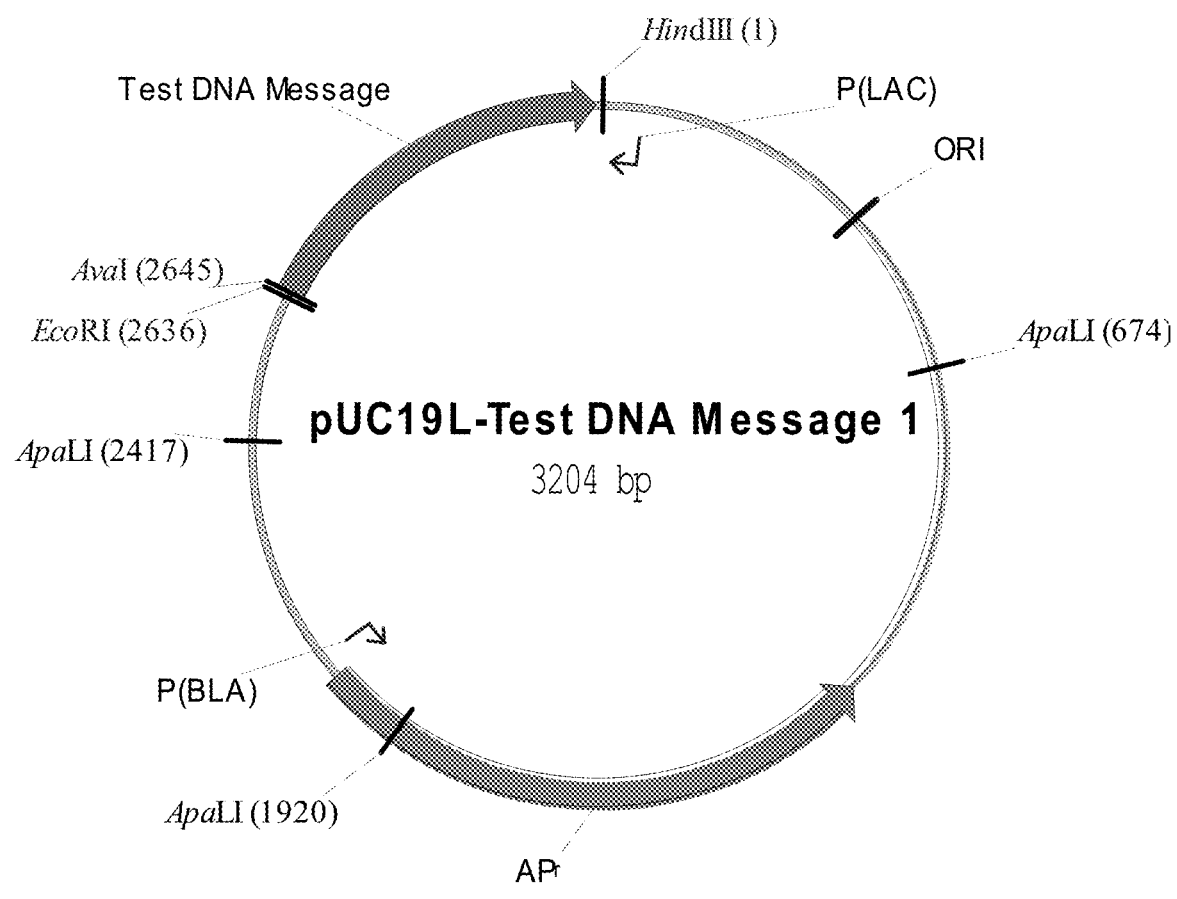
FIG. 6A-6B shows the results for encryption and decryption of the TM. Provided are the plasmid vector may for TM (FIG. 6A), was synthesized commercially, cloned into a plasmid vector, and transformed into E. coli. Gel electrophoresis (FIG. 6B) and subsequent DNA sequencing and back translation demonstrated the ability to successfully encode and retrieve the message stored in synthetic DNA.
Figure 6B:
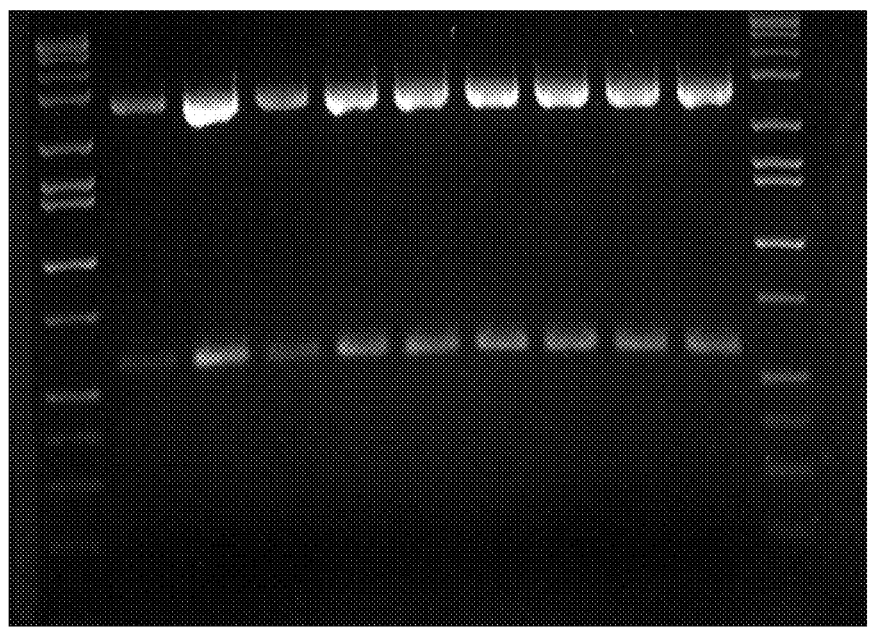

In an alternative strategy, the entire TM sequence was synthesized as one, double-stranded DNA (dsDNA) fragment of 651 bp in length (552 bp message with ~50-bp complimentary, overlapping 5' and 3' ends of the pUC19L vector). Using the Gibson Assembly® method (see, e.g., Gibson D G et al., "Enzymatic assembly of DNA molecules up to several hundred kilobases," *Nat. Methods* 2009; 6:343-5), 50 ng of the dsDNA TM fragment and 100 ng of the pUC19L vector were mixed with 10 µL of the Gibson Assembly® mix (New England Biolabs® Inc., NEB, Ipswich, MA) and incubated at 50° C. for 60 minutes. During this reaction, the exonucleases in the Gibson Assembly® mix digest the 5' DNA ends of the dsDNA. The complimentary DNA overhangs anneal, and the DNA polymerase extend the 3' ends, which results in a fully sealed construct (i.e., the TM fragment cloned into the pUC19L vector, FIG. 6A). The construct was then transformed into NEB 5-alpha Competent *E. coli* cells, and plated at 1:10 and 1:100 dilutions on LB agar plates with 100 µg/mL ampicillin and 40 µg/mL X-Gal. Plates were incubated overnight at 37° C. Ten white colonies were then inoculated into 5 mL of LB with ampicillin and grown overnight at 37° C. DNA was then isolated by mini-prepping and double digesting with EcoRI and HindIII. Gel electrophoresis yielded the correct band lengths of ~550 and ~2650 bp for the TM clones (FIG. 6B).

Plasmids from five of these clones were sent to Eurofins Genomics LLC (Louisville, KY) for sequencing with M13 forward and reverse primers, which flanked the TM fragment in the pUC13L vector. Sequencing confirmed the encrypted TM fragment was correct in all five plasmids. The translation key and the confirmed sequence were imported into EncrypDEMO and decrypted. The LDRD acknowledgement text was fully decrypted and translated correctly.

Overall, this initial prototype system provided proof-of-principle that the EncrypDEMO could encrypt messages and produce viable synthetic DNA fragments that could be cloned, sequenced and finally decrypted into original message.

Figure 7A:
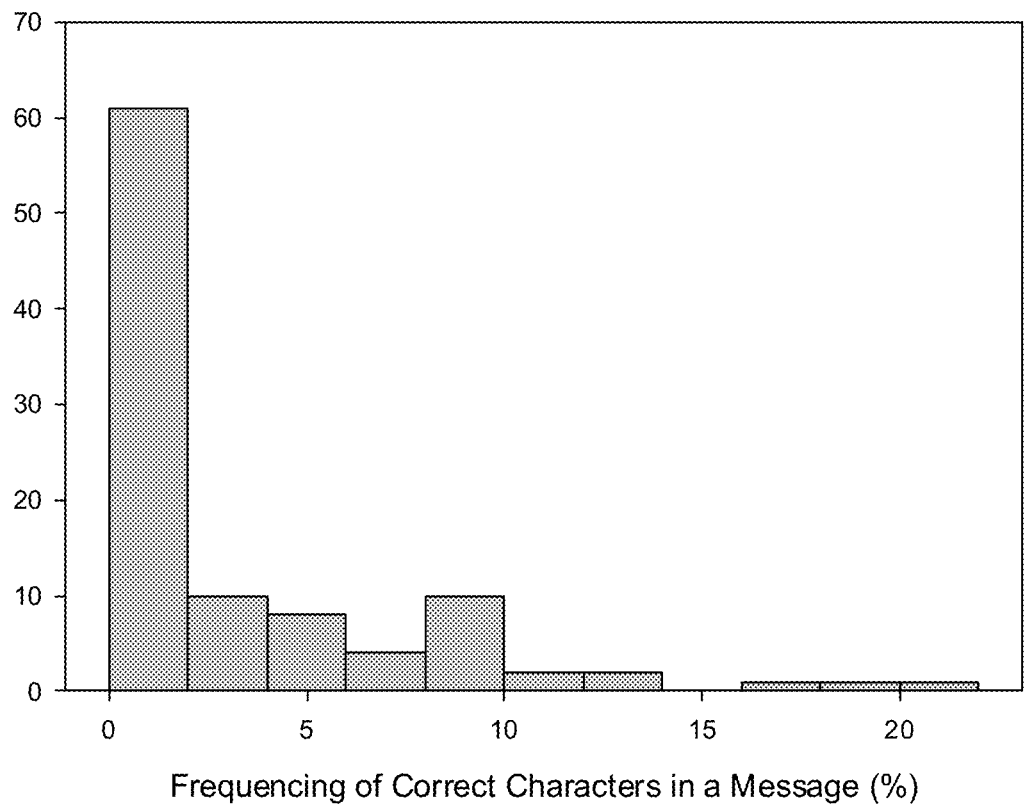

Further analysis was undertaken to understand the effect of using a random key to decrypt the encrypted message. For instance, decryption of the DNA sequence with a correct library of keys produced the plaintext message with 100% accuracy. However, decryption of the DNA sequence with random libraries (100 total) provided 32% of the decrypted message with 0 correct assignment. On average, with the improper translation key, an average of 2.7% of characters (~5 characters per decryption) were correctly assigned (median of 3%, maximum % correct characters of 20%) (FIG. 7A-7B). Also provided are examples of the output messages (FIG. 7C-7E) upon translation with a random (improper) key.

Example 6: DNA Encrypted Construct—Truman Letter

Figure 8D:
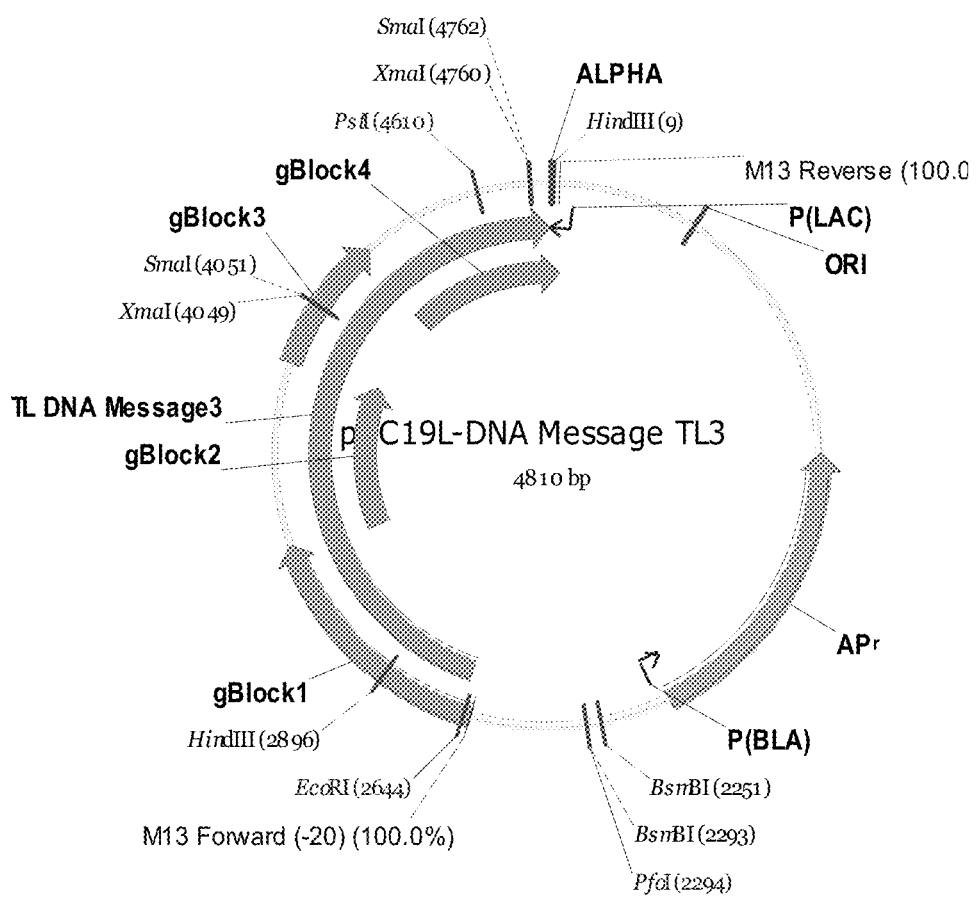

The second DNA message, called the Truman Letter (TL), was derived from a historical letter from President Harry S. Truman in which he asked the head of AT&T to assume management of Sandia National Laboratories as a separate and independent national laboratory. This message was composed of 717 characters with spaces (FIG. 8A). EncrypDEMO was used to generate a triple codon translation key (FIG. 8B), which was then used to encrypt and generate a 2,151-bp DNA sequence (FIG. 8C, SEQ ID NO:11). The sequence was longer than could be synthesized commercially in a single dsDNA block. As such, the sequence was subdivided into four dsDNA fragments (gBlock1 to gBlock4) ranging in size from 393 bp to 728 bp, all of which passed IDT's screening algorithm for synthesis.

Figure 8E:
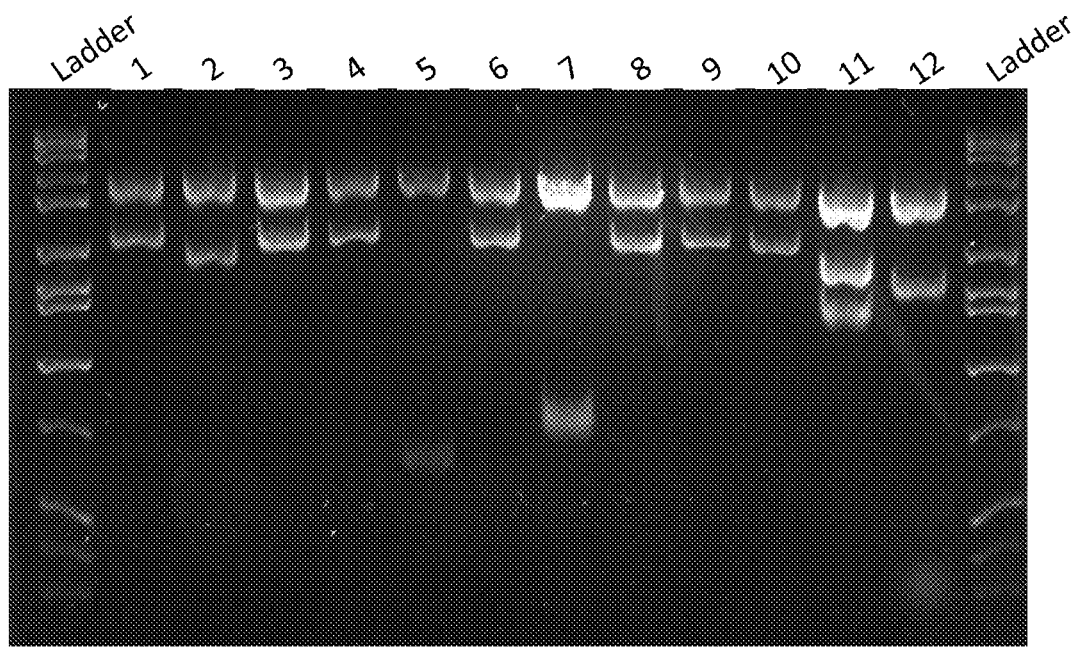

The dsDNA fragments were synthesized by IDT and cloned into a pUC19L vector (FIG. 8D) using the Gibson Assembly® method, as described herein. The reaction was transformed into NEB 5-alpha Competent *E. Coli* cells, mini-prepped and plasmids digested with HindIII to screen the clones for the correct fragment size. Seven of twelve clones digested correctly (bands of 1,923 and 2,887 bp, FIG. 8E) and were sent to Eurofins Genomics for sequencing.

Sequencing with the M13 Forward and Reverse primers did provide the entire 2,151 bp message; therefore, four additional primers were made and the entire clone was re-sequenced. The individual sequences were aligned in ContigExpress (part of Vector NTI Advance®, Invitrogen™) to generate a completed sequence covering the entire TL message. The sequenced message was inserted as input into the decryption software, and the TL Message was correctly reproduced without error as SEQ ID NO:11 (FIG. 8C).

Example 7: DNA Encrypted Construct—Dream Message

Figure 9D:
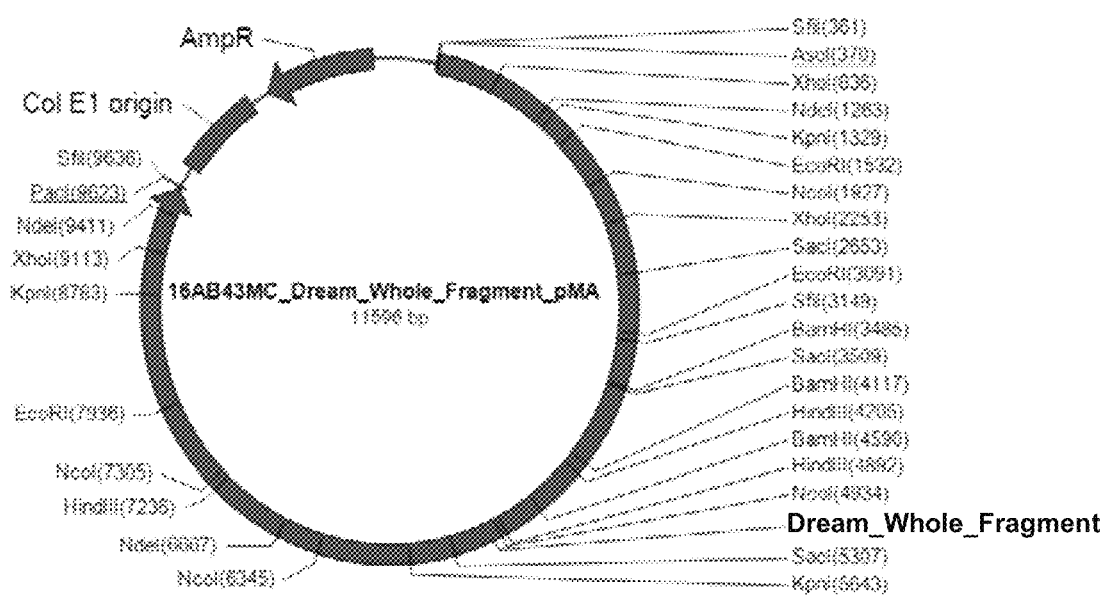

A third DNA construct was employed to demonstrate that a large amount of data could be encrypted and translated into DNA, synthesized, cloned, sequenced, and decrypted back into the original text. Dr. Martin Luther King Jr.'s speech "I Have a Dream" was selected because of its use of repetition and alliteration, which would provide an important test with respect to the ability of EncrypDEMO to produce DNA sequences capable of being synthesized. Text from the speech was edited and shortened to a 2,315-character (including spaces) text document called the "Dream Message" (DM, FIG. 9A). The text was then subdivided into five sections including ~560 to 670 characters per section. Each section was encrypted and translated into an encrypted message using EncrypDEMO, yielding nucleic acid sequences of 1,700 to 2,000 bp. A different translation key was generated by EncrypDEMO for each of the individual sections. This approach was used as a means of demonstrating enhanced security (e.g., more than one key needed to translate) and test the ability to reduce codon redundancy over long sequences. An example of keys is shown in FIG. 9C, and an example of translation of a section into DNA language is shown in FIG. 9B. The individual DNA sequence fragments were stitched together in silico, yielding a 9,240-bp DNA sequence containing the encrypted DM. The viability for synthesis of the DM sequence was verified by Life Technologies. Further, their screen confirmed that EncrypDEMO properly adjusted for other issues with synthesis such as the GC % content within boundaries of 20-70% and avoiding repetitive motifs and secondary structures. The DM sequence was synthesized by Life Technologies, and the DNA-encoded message was also cloned into vector pMA by Life Technologies, yielding a plasmid of 11,596 bp (FIG. 9D).

Figure 9E:
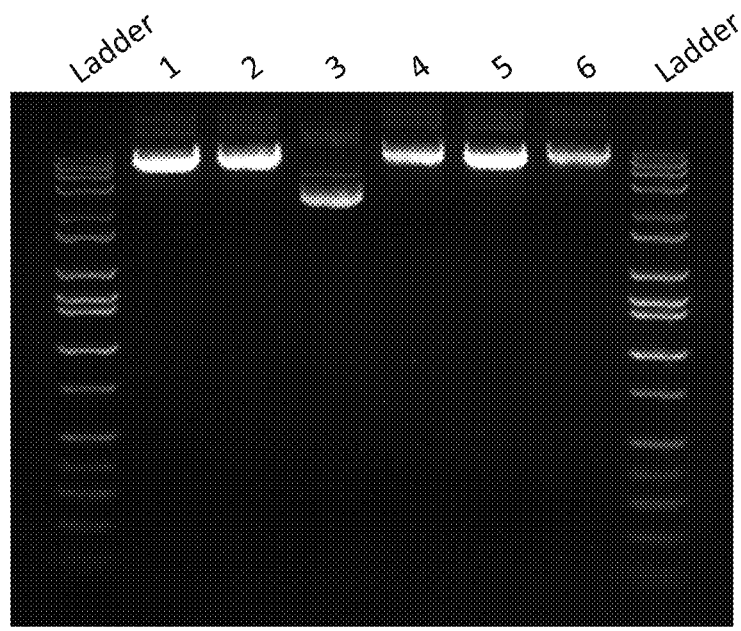

Following delivery of the plasmid containing the cloned DM, it was transformed into NEB 5-alpha Competent *E. coli* cells (see, FIG. 9E), mini-prepped as described above, and prepared for sequencing. A total of thirty primers (combination of forward and reverse) were designed and synthesized in order to sequence the entire region containing the DM. Sequencing was performed by Eurofins Genomics (one-day turn around), and data was imported into Contig-Express for assembly. The final DNA sequence was verified that the entire 9,240 bp Dream fragment was correctly synthesized and transformed into *E. coli*. Each of the five encrypted sections of the Dream fragment were then imported into EncrypDEMO and translated using the particular translation key for each fragment. Each decrypted segment was entered and combined into a text file reproducing the entire edited version of the "I Have a Dream" message without error.

Example 8: Recovery of Encrypted Message from Objects

Nucleic acid constructs were successfully recovered from surfaces of various objects. In one non-limiting instance, the Test Message (TM) plasmid (~1 µg) was placed on a nitrile glove and swabbed onto five laboratory surfaces in the following order: (1) phone, (2) pipette, (3) computer mouse, (4) confocal eye piece, and (5) lab bench. At the next day (~20 hours), the same surface areas were wiped with a cotton swab pre-moistened with deionized water (diH$_2$O). The swab tip was placed in 100 µl of Tris-EDTA (TE) and vortexed. Samples were incubated between 10 to 30 minutes, vortexed again, and centrifuged briefly to remove any larger material. PCR was performed using Phusion® High-Fidelity PCR reagents (NEB) using 2.5 µL of the DNA solution extracted from the various surface samples. PCR was also performed with a piece of the nitrile glove (~0.5 cm) used for swabbing the surface areas and a piece of scotch tape (~0.5 cm) with 1 ng of TM plasmid. These controls were used to determine if amplification of the TM DNA was possible using actual pieces of material in a PCR reaction.

Figure 10A:
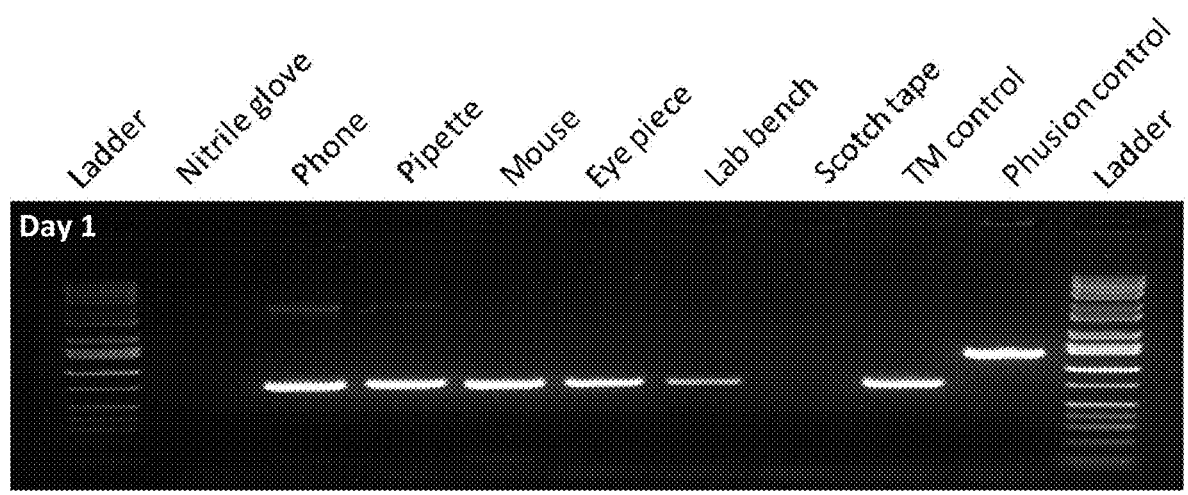
FIG. 10A-10B shows gel electrophoresis showing recovery of the Test Message (TM) from various surfaces. The TM was spotted on the different surfaces and swabbed. The swabs were then assayed by PCR to demonstrate the ability to recover the TM from the different surfaces. Provided are data for TM swabbed the following day (~20 hours after spotting, FIG. 10A) and after about 188 days (FIG. 10B).

Following DNA electrophoresis, the gel showed prominent bands for all swabbed lab surfaces (same size as TM control) with the fifth (final) surface touched (lab bench) having the lightest band (FIG. 10A). No bands were detected for either PCR samples containing the actual material of nitrile glove and scotch tape, suggesting that PCR could not be performed directly on these materials.

All laboratory surfaces were then cleaned with 70% isopropanol. On Day 84, the cleaned surfaces were again swabbed with cotton swabs pre-moistened with diH$_2$O. As described above, each swab was placed in 100 µl TE, vortexed briefly, incubated for 30 minutes and vortexed again. An aliquot (5 µL) of the swab solution was used for PCR amplification to test the ability to recover the TM from these surfaces. All lab surfaces were positive for the TM DNA after running a DNA gel electrophoresis on the amplified PCR samples.

Figure 10B:
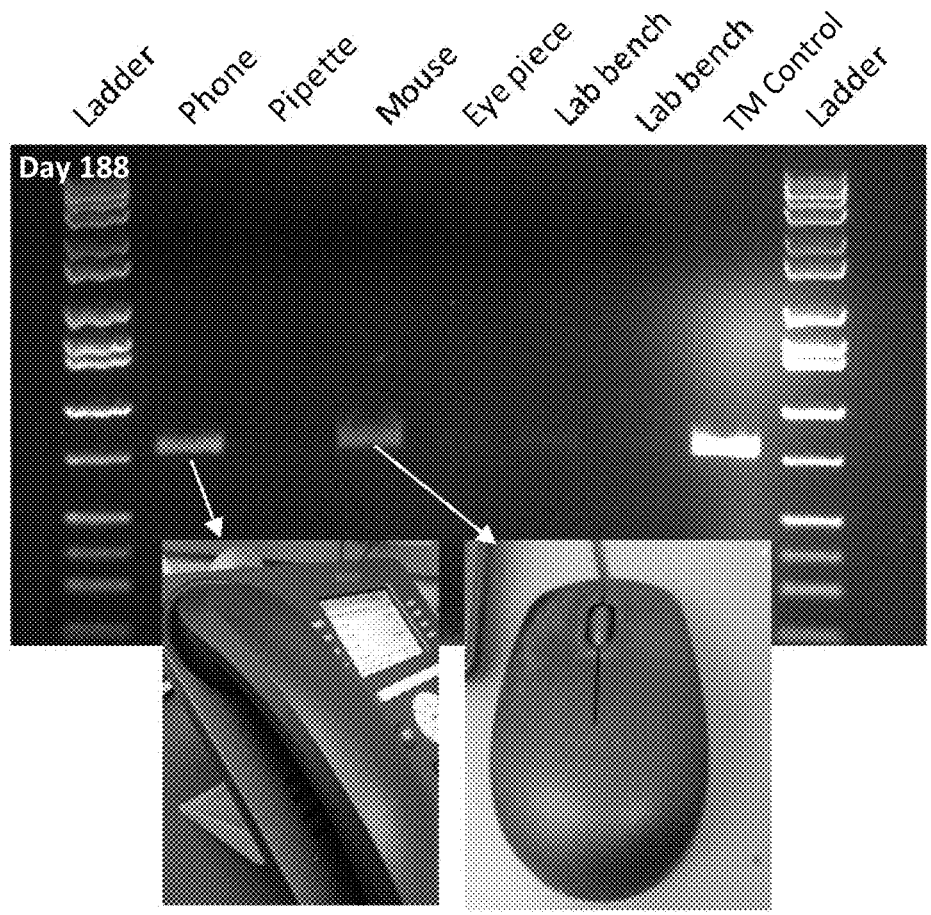

All surfaces were again cleaned with 70% isopropanol. The same protocol above was repeated at Day 188 for all six lab locations. The TM DNA was detected on the phone, computer mouse, and the lab bench after six months of laboratory usage and cleaning (FIG. 10B).

Example 9: Recovery of Encrypted Message Hidden in Paper

The TM DNA was also placed on a letter, which was then mailed cross-country to confirm that DNA could remain intact and detected after going through the rigors of the U.S. Postal Service (USPS). To confirm this hypothesis, 2 µL of the TM DNA plasmid (~600 ng) was placed on the letter and allowed to dry for 30 minutes. The letter was placed in a sealed plastic bag and mailed via the USPS from New Mexico to Pennsylvania, and then the letter was mailed back to New Mexico.

Figure 11:
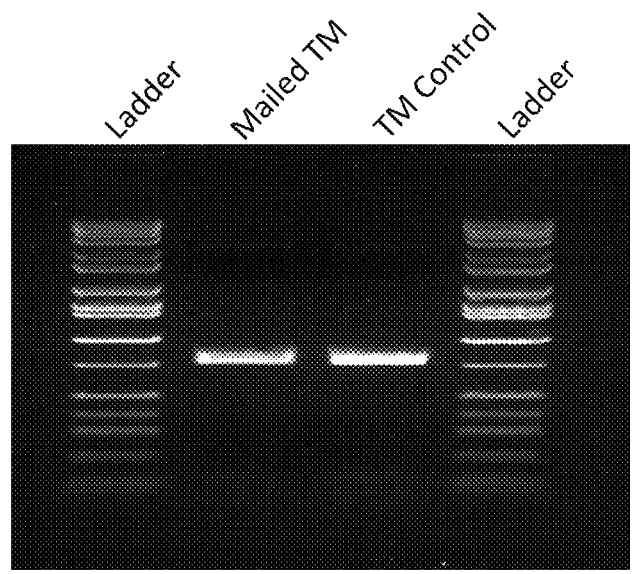
FIG. 11 shows recovery of TM DNA after being mailed cross-country. Provided is a DNA electrophoretic gel showing recovery of the TM DNA after the letter was mailed across the country and back.

The TM DNA was extracted approximately 2 weeks from placement of DNA on the mailed letter. A portion of the letter was excised and placed into a 1.5 mL microfuge tube with 50 µL of TE buffer. The sample was vortexed and incubated between 15 to 30 minutes at room temperature, vortexed again, and then centrifuged for 3 to 5 seconds. PCR was performed using Phusion® High-Fidelity reagents and polymerase and with 2.5 µL of the sample solution extracted from the letter. The TM plasmid (300 ng) was used as a positive control. A DNA band of the same size and prominence as the control plasmid was observed on the DNA electrophoresis gel (FIG. 11), verifying that the TM DNA could endure the cross-country trip and back by means of USPS.

Example 10: Watermarking Synthetic Materials with Encrypted Messages

Figure 12A:
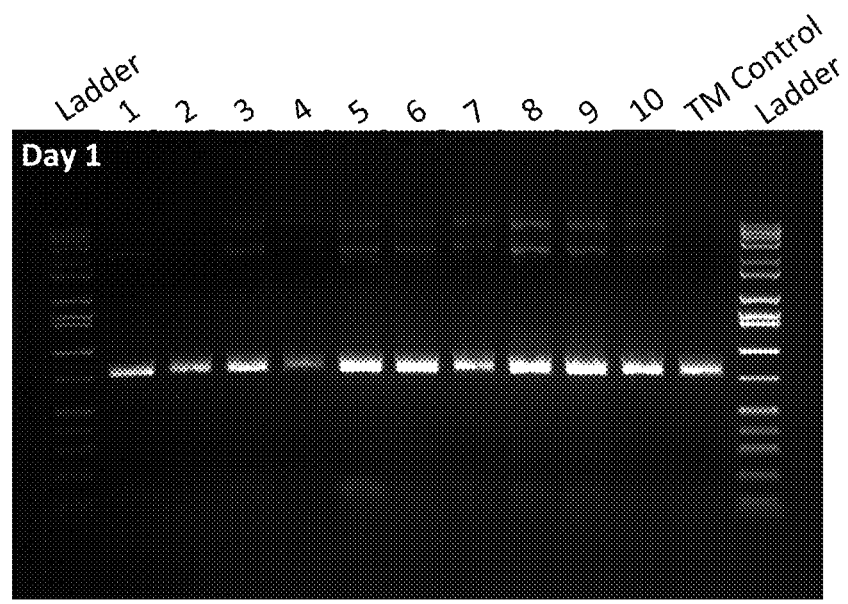
FIG. 12A-12C shows recovery of TM DNA from ten silicon rubber foam samples. Provided are DNA electrophoretic gels showing TM DNA bands recovered from silicon rubber foam samples on day 1 (FIG. 12A), 43 days after spotting (FIG. 12B), and 180 days after spotting (FIG. 12C).
Figure 12B:
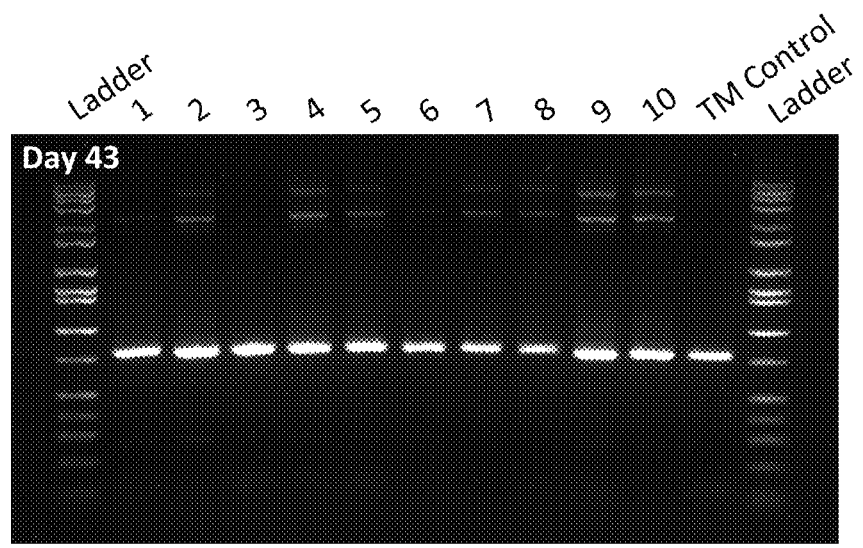
Figure 12C:
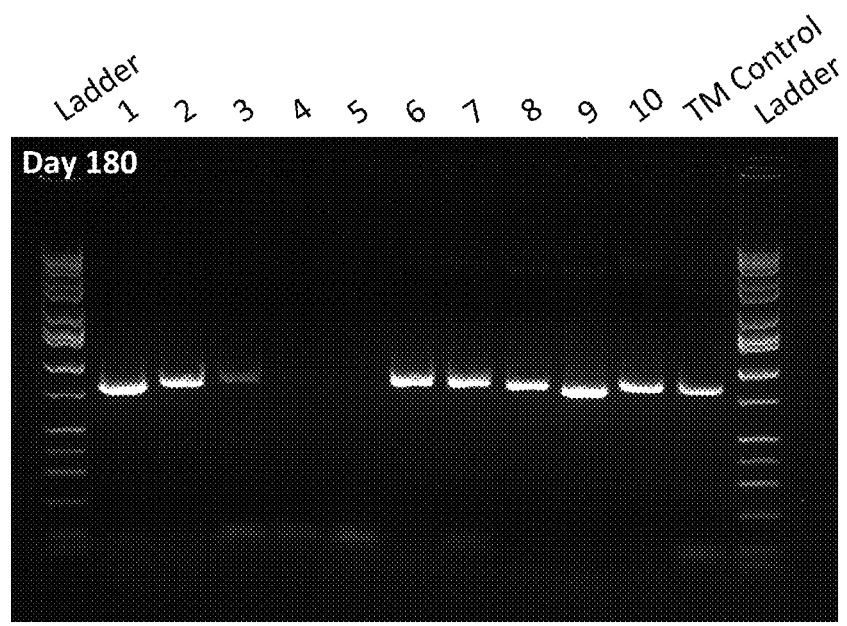

The ability to hide, or watermark, synthetic materials with encrypted messages was tested on ten samples of assorted silicone rubber foam materials. Each sample type of material was divided into three sections, and 150 ng of TM plasmid (0.5 µL) was spotted onto each of the sections. Following drying of the DNA solution, the foam samples were then stored at room temperature in a dry, dark location. DNA was extracted at Days 1, 43, and 180 on each sample type by slicing off a 0.5 to 0.75 cm section of the DNA embedded material. The excised materials were placed into a 1.5 mL microfuge tube with 50 µL of TE. Samples were vortexed briefly and incubated for 15 to 30 minutes at room temperature. Prior to the PCR, the samples were quickly vortexed again and centrifuged briefly to remove any large particles. Phusion® High Fidelity reagents and polymerase were used with 3 µL of each DNA sample solution and 1 µl (300 ng)

of TM control for PCR amplification. All material samples for Day 1 (FIG. 12A) and Day 43 (FIG. 12B) displayed a strong band corresponding to the TM DNA fragment. On day 180, eight of the ten samples gave visible bands on the gel (FIG. 12C).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

SEQUENCE LISTING

<160> NUMBER OF SEQ ID NOS: 13

<210> SEQ ID NO 1
<211> LENGTH: 582
<212> TYPE: DNA
<213> ORGANISM: Artificial Sequence
<220> FEATURE:
<223> OTHER INFORMATION: Synthetic construct

<400> SEQUENCE: 1

```
gtgaattcga gctcgagacc tgcggaacta gggagggtgt atgcttagtg acgcctatca      60
cattgctgac ctgcttgagc gtagctattt gcctcgctac gggtgaggct acgagcgggt     120
cctccgcatc tatcagctta gggcagggct ctattatgcc gggtgaggtg gagctgagcg     180
gtgtgcctat catgagtgag gagcggtgct ctaagctgcg cactaagaag gagctgcgaa     240
tgggcggaag aagcggtgtg ccgcctagat agcgaactac ggggctgcgc agctgcacta     300
tgacctaggg tgggcggtcc tctatcaagc tgcgcagcga gcctagccag ctgagcggtg     360
tgcagcccgc tagttagcaa agtgaggagc tgagtgaggg cggctgaaac gctagttagc     420
aaagtgagga gctgagtgag gcatctattt gcgagggctt agtgagctgc actaacagct     480
gaagctagca ggtagcctct acagctattt gctcaagctc cggtggggtg ggcttgctga     540
ctagggaggg tgggtaggag ctggcttatg caagcttggc gt                        582
```

<210> SEQ ID NO 2
<211> LENGTH: 582
<212> TYPE: DNA
<213> ORGANISM: Artificial Sequence
<220> FEATURE:
<223> OTHER INFORMATION: Synthetic construct

<400> SEQUENCE: 2

```
cacttaagct cgagctctgg acgccttgat ccctcccaca tacgaatcac tgcggatagt      60
gtaacgactg gacgaactcg catcgataaa cggagcgatg cccactccga tgctcgccca     120
ggaggcgtag atagtcgaat cccgtcccga gataatacgg cccactccac ctcgactcgc     180
cacacggata gtactcactc ctcgccacga gattcgacgc gtgattcttc ctcgacgctt     240
acccgccttc ttcgccacac ggcggatcta tcgcttgatg ccccgacgcg tcgacgtgat     300
actggatccc acccgccagg agatagttcg acgcgtcgct cggatcggtc gactcgccac     360
acgtcgggcg atcaatcgtt tcactcctcg actcactccc gccgactttg cgatcaatcg     420
tttcactcct cgactcactc cgtagataaa cgctcccgaa tcactcgacg tgattgtcga     480
cttcgatcgt ccatcggaga tgtcgataaa cgagttcgag gccaccccac ccgaacgact     540
gatccctccc acccatcctc gaccgaatac gttcgaaccg ca                        582
```

```
<210> SEQ ID NO 3
<211> LENGTH: 160
<212> TYPE: DNA
<213> ORGANISM: Artificial Sequence
<220> FEATURE:
<223> OTHER INFORMATION: Synthetic construct

<400> SEQUENCE: 3
gtgaattcga gctcgagacc tgcggaacta gggagggtgt atgcttagtg acgcctatca      60
cattgctgac ctgcttgagc gtagctattt gcctcgctac gggtgaggct acgagcgggt     120
cctccgcatc tatcagctta gggcagggct ctattatgcc                           160

<210> SEQ ID NO 4
<211> LENGTH: 140
<212> TYPE: DNA
<213> ORGANISM: Artificial Sequence
<220> FEATURE:
<223> OTHER INFORMATION: Synthetic construct

<400> SEQUENCE: 4
gggtgaggtg gagctgagcg gtgtgcctat catgagtgag gagcggtgct ctaagctgcg      60
cactaagaag gagctgcgaa tgggcggaag aagcggtgtg ccgcctagat agcgaactac     120
ggggctgcgc agctgcacta                                                 140

<210> SEQ ID NO 5
<211> LENGTH: 150
<212> TYPE: DNA
<213> ORGANISM: Artificial Sequence
<220> FEATURE:
<223> OTHER INFORMATION: Synthetic construct

<400> SEQUENCE: 5
tgacctaggg tgggcggtcc tctatcaagc tgcgcagcga gcctagccag ctgagcggtg      60
tgcagcccgc tagttagcaa agtgaggagc tgagtgaggg cggctgaaac gctagttagc     120
aaagtgagga gctgagtgag gcatctattt                                      150

<210> SEQ ID NO 6
<211> LENGTH: 117
<212> TYPE: DNA
<213> ORGANISM: Artificial Sequence
<220> FEATURE:
<223> OTHER INFORMATION: Synthetic construct

<400> SEQUENCE: 6
gcgagggctt agtgagctgc actaacagct gaagctagca ggtagcctct acagctattt      60
gctcaagctc cggtggggtg ggcttgctga ctagggaggg tgggtaggag ctggctt        117

<210> SEQ ID NO 7
<211> LENGTH: 151
<212> TYPE: DNA
<213> ORGANISM: Artificial Sequence
<220> FEATURE:
<223> OTHER INFORMATION: Synthetic construct

<400> SEQUENCE: 7
tcacccggca taatagagcc ctgccctaag ctgatagatg cggaggaccc gctcgtagcc      60
tcacccgtag cgaggcaaat agctacgctc aagcaggtca gcaatgtgat aggcgtcact     120
aagcatacac cctccctagt tccgcaggtc t                                    151

<210> SEQ ID NO 8
```

```
<211> LENGTH: 140
<212> TYPE: DNA
<213> ORGANISM: Artificial Sequence
<220> FEATURE:
<223> OTHER INFORMATION: Synthetic construct

<400> SEQUENCE: 8
aggtcatagt gcagctgcgc agccccgtag ttcgctatct aggcggcaca ccgcttcttc      60
cgcccattcg cagctccttc ttagtgcgca gcttagagca ccgctcctca ctcatgatag     120
gcacaccgct cagctccacc                                                 140

<210> SEQ ID NO 9
<211> LENGTH: 150
<212> TYPE: DNA
<213> ORGANISM: Artificial Sequence
<220> FEATURE:
<223> OTHER INFORMATION: Synthetic construct

<400> SEQUENCE: 9
cctcgcaaat agatgcctca ctcagctcct cactttgcta actagcgttt cagccgccct      60
cactcagctc ctcactttgc taactagcgg gctgcacacc gctcagctgg ctaggctcgc     120
tgcgcagctt gatagaggac cgcccaccct                                      150

<210> SEQ ID NO 10
<211> LENGTH: 126
<212> TYPE: DNA
<213> ORGANISM: Artificial Sequence
<220> FEATURE:
<223> OTHER INFORMATION: Synthetic construct

<400> SEQUENCE: 10
acgccaagct tgcataagcc agctcctacc caccctccct agtcagcaag cccacccccac     60 cggagcttga gcaaatagct gtagaggcta cctgctagct tcagctgtta gtgcagctca    120
ctaagc                                                                126

<210> SEQ ID NO 11
<211> LENGTH: 2151
<212> TYPE: DNA
<213> ORGANISM: Artificial Sequence
<220> FEATURE:
<223> OTHER INFORMATION: Synthetic construct

<400> SEQUENCE: 11
tgtactagag gtgctcgtgg tcttgctcct tggtccttgg ccgcatacgc tgtagctaga      60
tgcgcttggg cactcgccgg ttgcacttct gcttatacca gatatgctta taccactgct    120
agttatgcct gctggatagc tgtcgcaact ggtctgattg cttccgcctg ctgctggttg    180
ttgtgggccg cagcttgggc atatactgca tctttggctt atgccgctag attgtaagct    240
tataccagat atgcttatac cactgctggc acttcctccg ctaagagatt agccggtaga    300
tatgccggtt ggactttggc tagaataata actgagtatg ctccggcatc tactggtgct    360
atagccgcat atggtagaat atatgcttat accactgctt cttggggtac tatatattgg    420
gccgcagctg ccctcgctgg gagagcatct tggagagcta agagattagc cggtagatat    480
gccggtattg cttgggcagc tagttcctta ccgcatccga ctggtcatcc gactcacgct    540
tagactatcg ctcgtactat gtggatagcc cttgctacaa cctggttggc tgccgagact    600
ggtagatatt gggccgcaca cgctatcacc tggataaccg cttggttggc tagagctcga    660
tggtatagat ccgctttgac tctgtgcact gcatatgctg ccctcgctta taccactgct    720
```

```
agatatgcct gctggatagc tatcactaga gaggccgcat tggctgaggg tgccctgggt      780
agatgccacg cttggttggc tgccctcgct actatgtatg gtacttgcac tgcttggtgc      840
gaggccggtt atagagcaat aactgctaga gcatctgctc cgggtctgac tgcaataatt      900
gcttgggcag cttataccac tgctgcaaga tattgggccg caagatccgc ttctactctc      960
actgcattga ctcacgctag agcatctgct ttgaccgccc cgtcctctgc taccagacga     1020
actgcttata ccactgcttt aactttgtat gctgaggcct tgttgtggtt atccactgct     1080
tatactataa ccgcatggat aagatccgct tcttggggta ctatatattg ggccgcactt     1140
gctgtagcta ccgccgagac tgcttatacc agatatgcta gactctatac tggtgctatt     1200
gccccggcta ccagacgaac tgctaccact agaggttctg cttgcgccgg tactgcttct     1260
acttatagat ggtccgctct cggtgcctgc gcttatacca ctgctagtta tgcctgctgg     1320
atagctgtcg caactggtct gattgctttc gcctgctgct ggttgttgtg gccgcacac     1380 gctattgccc cgggtgctgc cggtctgaga gcatggagga gatattgggc cgcagctatc     1440
tggtcctccg ctctctgggc atctgcttgg tatgctgagg ccttgttgtg gttatccact     1500
gcttatgccg ctccggcatc tactggttat agataaactg cttataccac tgcttataga     1560
ttgtaacttg ctgtagcagc ttgcattgct gccgagtggg catgggccgc agctattgcc     1620
ccggctacca gacgaactgc taccactggt actgctagag cagctgccga ggaggccggt     1680
tatccggcat ggtatattgc ttatgccgct ggtactgcat ctactggtgc tagagcagct     1740
actatgataa ctgagtattg ggccgcaaga tccgctttga ctggtcgatg gataactgct     1800
tgggcagctt ataccactgc tgcaagatat tgggccgcaa gatccgcttg gcatatact      1860 ggtactttgt atcttgctgt agctagatgc gctatcggtt ggtattgggc actggctaga     1920
gctttgtggt gctggtccag aggtgctgca gcctatactg cttcttgggg tactatatat     1980
gcttatgccg cttgtggtct tgctgacctt gctgtccttg ctggcccgat ataatccact     2040
attcttgctc ggactggtat tgctttgtgg gcaataactg gtacttccat tgctattgcc     2100
ccgggtttgc acgctcgcag aggtggtatt gctacaggtc cgtgcagagc a             2151
```

<210> SEQ ID NO 12
<211> LENGTH: 1820
<212> TYPE: DNA
<213> ORGANISM: Artificial Sequence
<220> FEATURE:
<223> OTHER INFORMATION: Synthetic construct

<400> SEQUENCE: 12

```
gatttgctgg cgctttagta cgactcggtc tatagtcata taagtcagct gatactaact       60
gggtaaagtc tgtaaccggg tttcgggggt cgataggcat ccccccctaga ccaagagaag     120 aaccattaac agttacgtaa atgggatgac aatggccggc ctcgtcgaca tgcctgcctt      180
ggacctgcag gggtactcac taaatttatg atttggggaa cctcctggat gactagagag     240
tccactccgc ttgcgagcct gcagcgtgac ttagtcgagt aggctagact acttcccatt      300
tcataacatt agttatgtga acatggcaat acgggcgaga gcgtacgatc tcacccgcgg     360
cagcgctcac ggactcgtgt aattactagg agcgtaagct gctgtggaga gcctcaatcc     420
cttagtatta caattcgagg acctgaatcc agaagcctct cgagtatccc atattggcca     480
ggcttacgca ggctatacgc taggagcacc aaacactgtt caatggtgca atatgcccg      540 ggccgttccg ttcgtcagtg tcgcgataat attgacccgc atcgttaact aaatttcttc     600
```

```
agcgcagacg cattgacact cgcgtgcgac tgtatattgc gtgcgtgggt agaaaccatc      660
caaccgacag tttcgtgcta ccgtcggtta ccaccagaca tcagcgctga accgatagcc      720
gcgcttacag aaatgcttcg cgaatgaact tgaccggact tatttccgaa tatgctggcg      780
ataatcaatc gatcggctgt tagtcgcccc ggtttagtct tcccaactgg gtaaagcacg      840
taaccggggc cctaattcca gtcgaaatgt tgggggcaag gacccatatg tgtgggccca      900
gtaaccacta gccctgcttt aacgtctaga tcctgatact tctgcaaggt acccctcgga      960
aaccgatgtg atttctatta tgcactggat ctaagggtca gtttgcatcc ccggtactcc     1020
taagggaaat ggatgtaatg gagtgaaaca aggcctagga gattacattc atcgtggaag     1080
acggcacatt cctctttcac agtaaacacc tatgagtaga ctcggtgagg cagcagagag     1140
acaacatgag atgagaattc ggacggttgc ggggtcctag tgtaagcaac tccggcttag     1200
gctttgtatg taaggctaaa gtccactacc ttacgataca tacgctcagg ctagtgttat     1260
gtatcattgc tccgagttgg tgcaacctcc agatcatatc tggtctatgc gatatgatac     1320
acgctgtact ctggtaacac cgtctgcgcc atactttggt gccaagtcct acagcttagg     1380
tggtcagccg taaagaacag ccgtatagaa tagaatgtgg atcgccactg actgtttggt     1440
caatacgtac gtcccgagcg ccgcaattcg ttgagcaaac cctcgataac tgcggagctg     1500
cactatttct tcttgagtgc tggagtagga ggcgcattct ctaatataac catggcgaac     1560
aatcagaatt tcaccggcta ctgcaaggca accgaaaggg caggcggtgt gtatgaataa     1620
atatccaacg ctatcctgaa gggcaatgcg atctgttaat agccttcggg tgtctcgtct     1680
ttgcccaatc cgtcttgttt agttacccga aatgctgcgt atgtaagcaa cgtcggggcc     1740
tcgctagtca cggatcggtc ttaaaactgg gtgccccggg ggagtgtgga ttcccagtcg     1800
taccgttgta gccttgcaca                                                 1820

<210> SEQ ID NO 13
<211> LENGTH: 19
<212> TYPE: DNA
<213> ORGANISM: Artificial Sequence
<220> FEATURE:
<223> OTHER INFORMATION: Synthetic construct

<400> SEQUENCE: 13
tctacagggt agacccaca                                                    19
```

The invention claimed is:

1. A method for storing and transmitting information, the method comprising:
- converting each character in an information format into a triplet or quadruplet codon by employing a key, thereby generating an encrypted message represented by a nucleic acid or a complement thereof;
- synthesizing a nucleic acid construct comprising a lock region comprising a nucleic acid sequence with a primer binding region or a complement thereof, a translation key region comprising a nucleic acid sequence that corresponds to an identity of the key or a complement thereof, and a message region having a nucleic acid sequence comprising the encrypted message or a complement thereof;
- relaying the nucleic acid sequence of the lock region to a recipient and the key corresponding to the translation key region; and
- placing the nucleic acid construct on an object to be transmitted to the recipient;

wherein the synthesizing step further comprises:
- inserting a start codon indicating the beginning of the message region, and
- inserting a stop codon indicating the end of the message region.

2. The method of claim 1, wherein the synthesizing step further comprises:
- sectioning the nucleic acid construct, or a complement thereof, into a plurality of sections; and
- assembling each section by employing one or more of an exonuclease, a polymerase, and/or a ligase.

3. The method of claim 1, wherein the synthesizing step further comprises:
- inserting the nucleic acid construct into a vector; and
- expressing the vector.

4. The method of claim 1, further comprising:
- degrading the nucleic acid construct by 5. The method of claim 1, further comprising:
amplifying the nucleic acid construct by employing a polymerise, thereby generating a plurality of constructs.

6. The method of claim 5, further comprising:
determining the nucleic acid sequence of at least one of the plurality of constructs.

7. A nucleic acid construct comprising:
a lock region comprising a first primer binding region or a complement thereof;
a translation key region comprising a nucleic acid sequence that corresponds to an identity of a key or a complement thereof;
a message region comprising a nucleic acid sequence that corresponds to an encrypted message, wherein the encrypted message comprises an information format having each character that is converted into a triplet or quadruplet codon by employing the key, or a complement thereof,
a start region comprising a start codon, wherein the start region is in proximity to a 5' end of the message region; and
a stop region comprising a stop codon, wherein the stop region is in proximity to a 3' end of the message region,
wherein the key provides the identity of the start codon and the stop codon;
wherein the translation key region is disposed between the lock region and the message region.

8. The construct of claim 7, wherein the message region comprises a buffered message region comprising a nucleic acid sequence that interrupts the information format.

9. The construct of claim 8, further comprising:
a first leader region comprising a second primer binding region, wherein the leader region is in proximity to the 5' end of the construct;
an optional second leader region comprising a third primer binding region, wherein the second leader region is disposed between the translation key region and the message region; and
a trailer region comprising a fourth primer binding region, wherein the trailer region is in proximity to the 3' end of the construct.

10. The method of claim 1, wherein each character is one of an alphanumeric character, a symbol, a punctuation mark, and a space.

11. The method of claim 1, wherein the information format comprises a text, an image, or a matrix.

12. The method of claim 1, wherein the key comprises a different codon corresponding to a different character, and wherein the different codon comprises three nucleotides.

13. The method of claim 1, wherein the converting step comprises:
sectioning the information format into a plurality of sections; and
converting each character in each section with a different key, wherein each key comprises a different codon corresponding to a different character.

14. The method of claim 13, wherein the translation key region comprises a nucleic acid sequence that corresponds to the identity of each of the different keys.

15. The method of claim 1, wherein the converting step further comprises:
inserting one or more buffer regions in the encrypted message or a complement thereof, wherein each buffer region comprises a nucleic acid sequence that interrupts the information format, thereby generating a buffered, encrypted message represented by a plurality of nucleotides.

16. The method of claim 1, wherein the lock region comprises of from about 15 to about 35 nucleotides.

17. The method of claim 1, wherein the translation key region comprises of from about 15 to about 35 nucleotides.

18. The method of claim 1, wherein the nucleic acid construct comprises a single-stranded sequence or a double-stranded sequence.

19. The construct of claim 7, wherein the key comprises a different codon corresponding to a different character.

20. The construct of claim 7, wherein each character is one of an alphanumeric character, a symbol, a punctuation mark, and a space.

* * * * *